United States Patent
Seok et al.

(10) Patent No.: US 11,952,372 B2
(45) Date of Patent: Apr. 9, 2024

(54) TRIBENZAZOLE AMINE DERIVATIVE AND ORGANIC ELECTROLUMINESCENT DEVICE COMPRISING SAME

(71) Applicant: LAPTO CO., LTD., Seongnam-si (KR)

(72) Inventors: Moon-ki Seok, Seongnam-si (KR); Byung-soo Go, Seongnam-si (KR); Chul-soo Lim, Seongnam-si (KR); Hyun-a Kim, Seongnam-si (KR); Kyou-sic Kim, Seongnam-si (KR); Yong-pil Park, Seongnam-si (KR); Kap-jong Han, Seongnam-si (KR); Eu-gene Oh, Seongnam-si (KR)

(73) Assignee: LAPTO CO., LTD., Seongnam-si (KR)

( * ) Notice: Subject to any disclaimer, the term of this patent is extended or adjusted under 35 U.S.C. 154(b) by 416 days.

(21) Appl. No.: 17/296,442

(22) PCT Filed: Aug. 30, 2019

(86) PCT No.: PCT/KR2019/011129
§ 371 (c)(1),
(2) Date: May 24, 2021

(87) PCT Pub. No.: WO2020/122359
PCT Pub. Date: Jun. 18, 2020

(65) Prior Publication Data
US 2022/0017503 A1 Jan. 20, 2022

(30) Foreign Application Priority Data

Dec. 12, 2018 (KR) .................. 10-2018-0160253

(51) Int. Cl.
*H01L 29/08* (2006.01)
*C07D 413/14* (2006.01)
(Continued)

(52) U.S. Cl.
CPC ......... *C07D 413/14* (2013.01); *C07D 417/14* (2013.01); *H10K 85/633* (2023.02);
(Continued)

(58) Field of Classification Search
CPC .. C07D 413/14; C07D 417/14; H10K 85/633; H10K 50/16; H10K 50/11; H10K 50/171;
(Continued)

(56) References Cited

FOREIGN PATENT DOCUMENTS

CN 105440084 A 3/2016
EP 1 191 821 A1 3/2002
(Continued)

OTHER PUBLICATIONS

Xiaolong Yang, et al., "Achieving High-Performance Solution-Processed Orange OLEDs with the Phosphorescent Cyclometalated Trinuclear Pt(II) Complex", American Chemical Society (ACS) Applied Materials & Interfaces, Mar. 5, 2018, vol. 10, pp. 10227-10235.
(Continued)

*Primary Examiner* — Niki H Nguyen
(74) *Attorney, Agent, or Firm* — Sughrue Mion, PLLC

(57) ABSTRACT

Provided is a tribenzazole amine derivative represented by Formula 1 that effectively absorbs high energy UV light from an external light source to minimize damage to organic materials present in an organic electroluminescent device, contributing to a substantial improvement in the lifetime of the organic electroluminescent device. Also provided is an organic electroluminescent device using the tribenzazole amine derivative. The organic electroluminescent device includes a first electrode, a second electrode, and an organic layer arranged between the first and second electrodes. The organic layer includes the tribenzazole amine derivative.

6 Claims, 2 Drawing Sheets

(51) Int. Cl.
*C07D 417/14* (2006.01)
*H10K 85/60* (2023.01)
*H10K 50/11* (2023.01)
*H10K 50/15* (2023.01)
*H10K 50/16* (2023.01)
*H10K 50/17* (2023.01)
*H10K 50/844* (2023.01)

(52) U.S. Cl.
CPC .............. *H10K 50/11* (2023.02); *H10K 50/15* (2023.02); *H10K 50/16* (2023.02); *H10K 50/171* (2023.02); *H10K 50/844* (2023.02)

(58) Field of Classification Search
CPC .... H10K 50/844; H10K 50/15; H10K 85/631; H10K 50/17; H10K 85/6572; H10K 50/00; H10K 85/654; H10K 85/324; H10K 85/626; H10K 2102/351; H10K 50/18; H10K 50/81; H10K 85/111; H10K 59/35; H10K 50/125; H10K 85/1135; H10K 85/115; H10K 85/60; H10K 85/6565; H10K 50/818; H10K 50/865; H10K 85/40; H10K 50/826; H10K 85/6576; H10K 85/311; H10K 85/649; H10K 2101/30; H10K 50/12; H10K 50/19; H10K 50/80; H10K 85/6574; H10K 2101/40; H10K 50/156; H10K 59/38; H10K 85/00; H10K 59/00; H10K 71/135; H10K 50/166; H10K 50/816; H10K 85/701; H10K 2101/90; H10K 71/611; H10K 85/341; H10K 2101/00; H10K 2102/00; H10K 2102/331
See application file for complete search history.

(56) References Cited

FOREIGN PATENT DOCUMENTS

| | | | | |
|---|---|---|---|---|
| EP | 1191821 A1 | * | 3/2002 | ............. C09K 11/06 |
| KR | 10-0861168 B1 | | 9/2008 | |
| KR | 10-2016-0062307 A | | 6/2016 | |
| WO | WO-2006045201 A2 | * | 5/2006 | ............. B82Y 10/00 |

OTHER PUBLICATIONS

Hai-Ying Wang, et al., "Synthesis and characterization of triphenylamine-benzothiazole-based donor and acceptor materials", Synthetic Metals, 2010, vol. 160, pp. 1065-1072.

International Searching Report, International Search Report for PCT/KR2019/011129 dated Dec. 23, 2019 (PCT/ISA/210).

* cited by examiner

TRIBENZAZOLE AMINE DERIVATIVE AND ORGANIC ELECTROLUMINESCENT DEVICE COMPRISING SAME

CROSS REFERENCE TO RELATED APPLICATIONS

This application is a National Stage of International Application No. PCT/KR2019/011129 filed Aug. 30, 2019, claiming priority based on Korean Patent Application No. 10-2018-0160253 filed Dec. 12, 2018.

TECHNICAL FIELD

The present invention relates to a tribenzazole amine derivative and an organic electroluminescent device including the tribenzazole amine derivative. More particularly, the present invention relates to a tribenzazole amine derivative and an organic electroluminescent device including a capping layer in which the tribenzazole amine derivative is used to achieve both high refractive index and ultraviolet absorptivity.

BACKGROUND ART

With the recent trend toward large-sized displays, there is an increasing demand in the display industry for flat display devices that take up small spaces. Liquid crystal displays (LCDs) have a limited viewing angle and require additional light sources because they are not self-luminous. For these reasons, self-luminous organic light emitting diodes (OLEDs) have attracted attention as promising displays.

In 1963, Pope et al. have conducted the first research on carrier injection electroluminescence (EL) utilizing a single crystal of an anthracene aromatic hydrocarbon in the field of OLEDs. Based on this research, basic mechanisms such as charge injection, recombination, exciton formation, and light emission in organic materials, and luminescent properties have been understood and studied.

Particularly, various approaches aimed at increasing the luminescent efficiency of devices have been proposed in connection with changes in the structure of devices and the development of device materials (Sun, S., Forrest, S. R., Appl. Phys. Lett. 91, 263503 (2007)/Ken-Tsung Wong, Org. Lett., 7, 2005, 5361-5364).

A typical OLED display basically has a multilayer structure consisting of an anode, a hole injection layer (HIL), a hole transporting layer (HTL), an emission layer (EML), an electron transporting layer, and a cathode. That is, the OLED display has a structure in which an organic multilayer film is sandwiched between both electrodes.

In general, organic luminescence refers to a phenomenon in which organic materials are used to convert electrical energy into light energy. An organic light emitting device using organic luminescence usually has a structure including an anode, a cathode, and an organic layer interposed therebetween. The organic layer often consists of one or more layers composed of different materials to increase the efficiency and stability of the organic light emitting device. For example, the organic layer may include a hole injection layer, a hole transporting layer, an emission layer, an electron transporting layer, and an electron injection layer.

When a voltage is applied between the two electrodes of the organic light emitting device, holes and electrons are injected into the organic layer from the anode and the cathode, respectively. The holes recombine with the electrons in the organic layer to form excitons. The excitons fall to the ground state to emit light. Such organic light emitting devices are known to have many advantages, including self-luminescence, high luminance, high efficiency, low driving voltage, wide viewing angle, high contrast, and fast response.

Materials for organic layers of organic light emitting devices can be classified into light emitting materials and charge transporting materials, for example, hole injection materials, hole transporting materials, electron transporting materials, and electron injection materials, by their functions.

Light emitting materials include blue, green, and red light emitting materials that emit different colors of light and yellow and orange light emitting materials that are necessary to obtain more natural colors. Other light emitting materials are host/dopant systems that can be used to achieve high color purity and enhance luminescent efficiency through energy transfer. The principle is that when a small amount of a dopant, whose energy band gap is smaller and whose luminescent efficiency is higher than those of a host as a main material for an emission layer, is introduced into the emission layer, excitons generated from the host are transported to the dopant to emit light with high efficiency. At this time, since the wavelength of the host is shifted to the wavelength band of the dopant, light of a desired wavelength can be obtained depending on the type of the dopant.

Materials for organic layers of organic light emitting devices, for example, hole injection materials, hole transporting materials, light emitting materials, electron transporting materials, and electron injection materials, have been developed to achieve excellent characteristics of the devices. Organic light emitting devices using recently commercialized materials for organic layers have been recognized for their performance.

However, since the commercialization of organic light emitting devices, characteristics other than the luminescent properties of organic light emitting devices have been taken into consideration.

Most organic light emitting devices are exposed to external light sources for a long time and thus remain exposed to high-energy UV light, which continuously affects organic materials constituting the organic light emitting devices. This problem can be solved by applying UV-absorbing capping layers to organic light emitting devices to prevent their exposure to high-energy light sources.

A typical organic light emitting device is known to have a wide viewing angle but undergoes a large variation in terms of light source's spectrum depending on the viewing angle. This is due to a deviation between the total refractive index of constituent elements and materials (e.g., a glass substrate, organic materials, and electrode materials) of the organic light emitting device and an optimal refractive index depending on the emission wavelength of the organic light emitting device.

Generally, a high refractive index is required for blue light emission and a lower refractive index is required for a longer wavelength. There is thus a need to develop a material for a capping layer that simultaneously meets the aforementioned requirements in terms of UV absorption characteristics and optimal refractive index.

The efficiency of an organic light emitting device can be generally divided into internal luminescent efficiency and external luminescent efficiency. The internal luminescent efficiency is related to the formation efficiency of excitons in the organic layer for photoconversion.

The external luminescent efficiency refers to the emission efficiency of light from the organic layer outside the organic light emitting device.

Not only high internal luminescent efficiency but also high external luminescent efficiency is required to raise the overall efficiency. Thus, there is a need to develop a compound for a capping layer (CPL) that has new functions to achieve high external luminescent efficiency and prevent many problems caused by long-term exposure to daylight. Particularly, there is a need to develop a material for a capping layer (CPL) that has an outstanding ability to absorb light in a UV wavelength band.

DETAILED DESCRIPTION OF THE INVENTION

Problems to be Solved by the Invention

One object of the present invention is to provide a material for a capping layer of an organic light emitting device that can be used to improve the luminescent efficiency and lifetime of the organic light emitting device while achieving improved viewing angle characteristics.

A further object of the present invention is to provide an organic light emitting device that employs a capping layer to achieve its improved characteristics.

Means for Solving the Problems

One embodiment of the present invention provides an organic electroluminescent device including a first electrode, an organic layer arranged on the first electrode, a second electrode arranged on the organic layer, and a capping layer arranged on the second electrode wherein the organic layer includes a tribenzazole amine derivative represented by Formula 1:

[Formula 1]

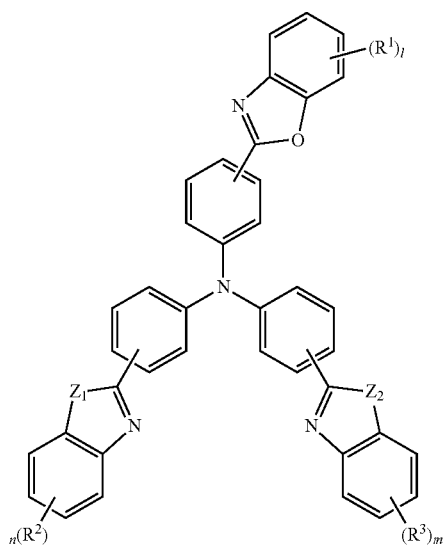

wherein $Z_1$ and $Z_2$ are each independently O or S, $R^1$, $R^2$, and $R^3$ are identical to or different from each other and are each independently hydrogen, deuterium, substituted or unsubstituted alkyl, substituted or unsubstituted cycloalkyl, substituted or unsubstituted alkoxy, substituted or unsubstituted aryloxy, substituted or unsubstituted aralkyl, substituted or unsubstituted alkylaryl, substituted or unsubstituted allyl or substituted or unsubstituted heteroaryl, and l, n, and m are integers from 0 to 4.

The organic layer of the organic electroluminescent device may include a hole transporting region, an emission layer disposed on the hole transporting region, and an electron transporting region disposed on the emission layer; and the capping layer may include the tribenzazole amine derivative represented by Formula 1.

The present invention also provides the tribenzazole amine derivative represented by Formula 1.

Effects of the Invention

The presence of the capping layer in the organic electroluminescent device of the present invention can minimize damage to organic materials in the organic electroluminescent device by an external light source due to the ability of the capping layer to absorb UV light, so that the inherent efficiency and lifetime of the organic electroluminescent device can be maintained as much as possible.

In addition, the use of the capping layer in the organic electroluminescent device of the present invention can lead to an improvement in light efficiency, a reduction in the full width at half maximum of the emission spectrum, and an increase in viewing angle such that the organic electroluminescent device of the present invention has characteristics comparable to currently commercially available organic electroluminescent devices.

BEST MODE FOR CARRYING OUT THE INVENTION

Figure 1:
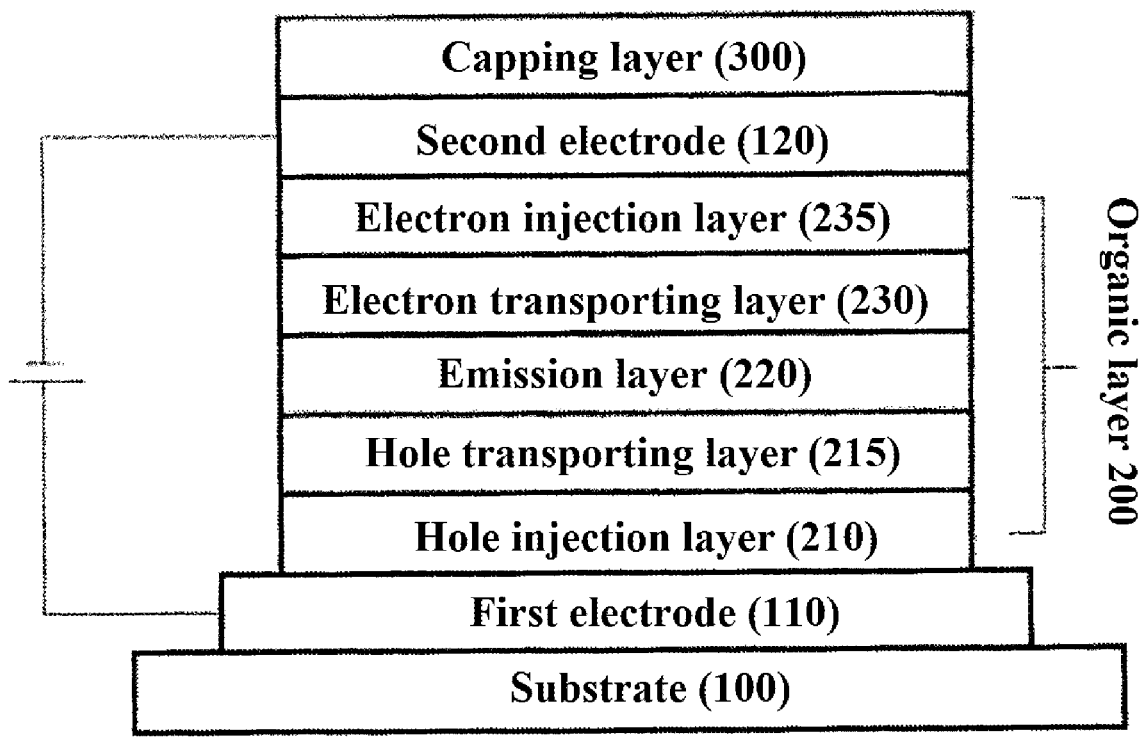
FIG. 1 is a schematic cross-sectional view of an organic electroluminescent device according to one embodiment of the present invention.

As the present invention allows for various changes and numerous embodiments, particular embodiments will be illustrated in drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention.

As used herein, the term "substituted" in the definition of "substituted or unsubstituted" refers to substitution with at least one substituent selected from the group consisting of deuterium and halogen atoms and cyano, nitro, amino, hydroxyl, silyl, boron, phosphine oxide, phosphine sulfide, alkyl, haloalkyl, alkoxy, alkenyl, aryl, heteroaryl, and heterocyclic groups. The term "unsubstituted" in the same definition indicates having no substituent. Each of the substituents exemplified above may be optionally further substituted. For example, a biphenyl group may be interpreted as an aryl group or a phenyl group substituted with a phenyl group.

Examples of the halogen atoms include fluorine, chlorine, bromine, and iodine atoms.

The alkyl groups may be linear, branched or cyclic. The number of carbon atoms in each of the alkyl groups is 1 to 50, preferably 1 to 6. Examples of the alkyl groups include, but are not limited to, methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, and n-triacontyl groups.

As used herein, the term "cyclic hydrocarbon group" refers to any functional group or substituent derived from an alicyclic hydrocarbon. The cyclic hydrocarbon group may be a saturated cyclic hydrocarbon group having 5 to 20 ring carbon atoms.

As used herein, the term "aryl group" refers to any functional group or substituent derived from an aromatic cyclic hydrocarbon ring. The aryl group may be monocyclic or polycyclic. The number of ring carbon atoms in the aryl group may be 6 to 30, preferably 6 to 15. Examples of such aryl groups include, but are not limited to, phenyl, naphthyl, fluorenyl, anthracenyl, phenanthryl, biphenyl, terphenyl, quaterphenyl, quinquephenyl, sexiphenyl, triphenylenyl, pyrenyl, perylenyl, naphthacenyl, benzofluoranthenyl, and chrysenyl groups.

The fluorenyl group may be substituted. In this case, two substituents may be bonded to each other to form a spiro structure.

The heteroaryl group may be interrupted by one or more heteroatoms selected from O, N, P, Si, and S. The N and S atoms may be optionally oxidized and the N atom(s) may be optionally quaternized. The number of ring carbon atoms in the heteroaryl group is 2 to 30 or 2 to 20. The heteroaryl group may be monocyclic or polycyclic. For example, the polycyclic heteroaryl group may have a bicyclic or tricyclic structure.

Examples of such heteroaryl groups include, but are not limited to, thiophenyl, furanyl, pyrrolyl, imidazolyl, pyrazolyl, thiazolyl, oxazolyl, oxadiazolyl, triazolyl, pyridinyl, bipyridinyl, pyrimidinyl, triazinyl, tetrazinyl, triazolyl, tetrazolyl, acridyl, pyridazinyl, pyrazinyl, quinolinyl, quinazolinyl, quinoxalinyl, phenoxazinyl, phthalazinyl, pyridopyrimidinyl, pyridopyrazinopyrazinyl, isoquinolinyl, cinnolinyl, indolyl, isoindolyl, indazolyl, carbazolyl, N-arylcarbazolyl, N-heteroarylcarbazolyl, N-alkylcarbazolyl, benzoxazolyl, benzoimidazolyl, benzothiazolyl, benzocarbazolyl, benzothiophenyl, benzoisothiazolyl, benzoisoxazolyl, dibenzothiophenyl, benzofuranyl, phenanthrolinyl, phenanthridinyl, thiazolyl, isoxazolyl, oxadiazolyl, thiadiazolyl, isothiazolyl, phenothiazinyl, benzodioxolyl, dibenzosilolyl, dibenzofuranyl, and isobenzofuranyl groups. An N-oxide aryl group may correspond to the monocyclic or polycyclic heteroaryl group. The N-oxide aryl group may be, for example, a quaternary salt such as a pyridyl N-oxide or quinolyl N-oxide group but is not limited thereto.

As used herein, the term "silyl group" is intended to include alkylsilyl and arylsilyl groups. Examples of such silyl groups include, but are not limited to, trimethylsilyl, triethylsilyl, t-butyldimethylsilyl, vinyldimethylsilyl, propyldimethylsilyl, triphenylsilyl, diphenylsilyl, and phenylsilyl groups.

As used herein, the term "boron group" is intended to include alkyl boron and aryl boron groups. Examples of such boron groups include, but are not limited to, trimethyl boron, triethyl boron, t-butyl dimethyl boron, triphenyl boron, diphenyl boron, and phenyl boron groups.

The alkenyl groups may be linear or branched. The number of carbon atoms in each of the alkeyl groups is 2 to 30, preferably 2 to 10, but is not particularly limited thereto. Examples of the alkenyl groups include, but are not limited to, vinyl, 1-butenyl, 1-pentenyl, 1,3-butadienyl, allyl, styrenyl, and styrylvinyl groups.

As used herein, the term "adjacent group" may mean a substituent on an atom directly attached to an atom substituted with the corresponding substituent, another substituent on an atom substituted with the corresponding substituent or a substituent disposed sterically closest to the corresponding substituent. For example, the two methyl groups in 1,2-dimethylbenzene can be interpreted as "adjacent groups" and the two ethyl groups in 1,1-diethylcyclopentene can be interpreted as "adjacent groups".

Exemplary embodiments of the present invention will now be described with reference to FIGS. 1 and 2.

Figure 2:
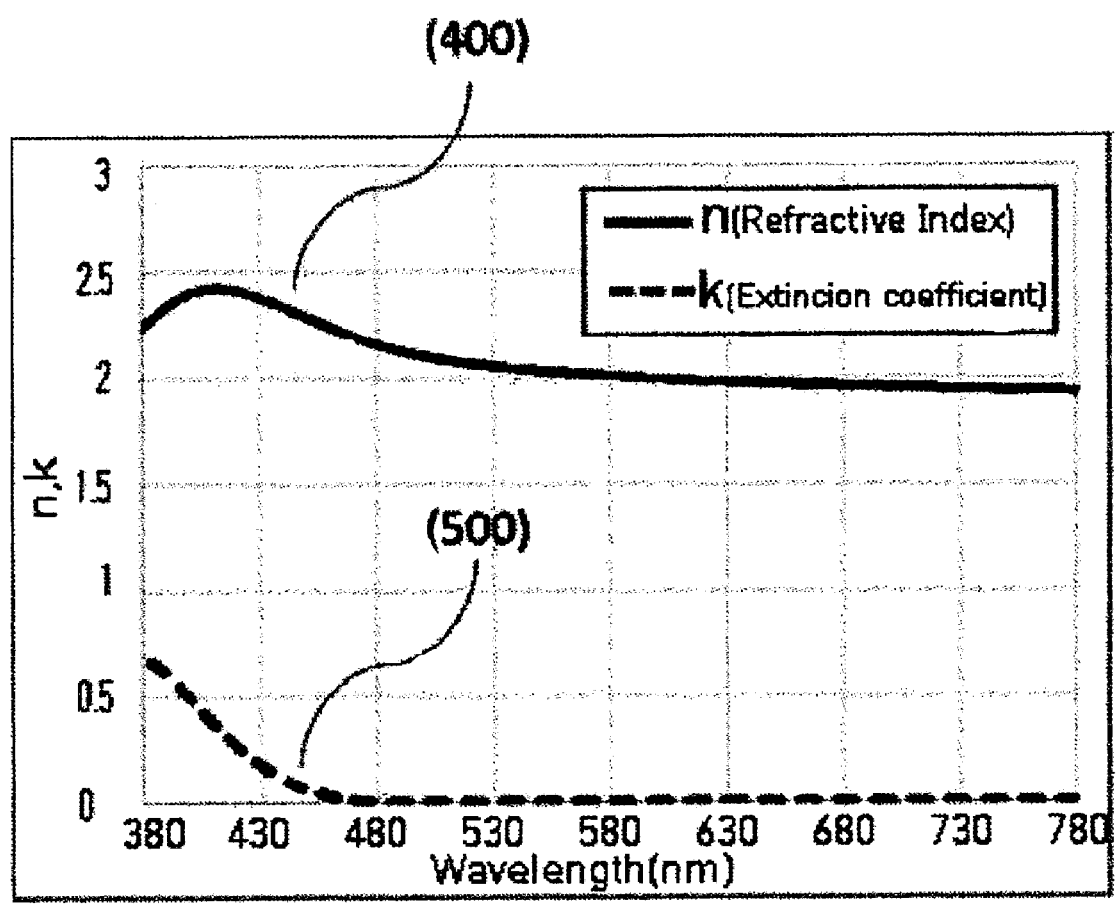
FIG. 2 shows exemplary characteristics of a material of the present invention.

FIG. 1 is a schematic cross-sectional view of an organic electroluminescent device according to one embodiment of the present invention. Referring to FIG. 1, the organic electroluminescent device includes a first electrode 110, a hole injection layer 210, a hole transporting layer 215, an emission layer 220, an electron transporting layer 230, an electron injection layer 235, a second electrode 120, and a capping layer 300 stacked in this order on a substrate 100.

The first electrode 110 and the second electrode 120 are arranged opposite to each other and an organic layer 200 is arranged therebetween. The hole injection layer 210, the hole transporting layer 215, the emission layer 220, the electron transporting layer 230, and the electron injection layer 235 together form the organic layer 200.

The capping layer 300 is a feature of the present invention. The capping layer 300 is a functional layer deposited on the second electrode 120 and includes an organic material represented by Formula 1.

In the organic electroluminescent device illustrated in FIG. 1, the first electrode 110 is a conductive electrode and may be made of a metal alloy or a conductive material. The first electrode 110 is generally an anode but its function as an electrode is not limited.

The first electrode 110 may be prepared by depositing an electrode material on the substrate 100. Alternatively, electron beam evaporation or sputtering may be used instead of deposition. The material for the first electrode 110 may be selected from high work function materials that facilitate the injection of holes into the organic electroluminescent device.

The capping layer 300 is provided when the organic electroluminescent device is of a top emission type. In this case, a reflective electrode is used as the first electrode 110. Suitable materials for the first electrode include metals and alloys rather than oxides, for example, magnesium (Mg), aluminum (Al), aluminum-lithium (Al—Li), calcium (Ca), magnesium-indium (Mg—In), and magnesium-silver (Mg—Ag). Carbon-based flexible materials such as carbon nanotubes (CNTs) and graphene have also been used in recent years.

The organic layer 200 may consist of a plurality of layers. In this case, the organic layer 200 may include a hole transporting region 210-215 arranged on the first electrode 110, an emission layer 220 arranged on the hole transporting region, and an electron transporting region 230-235 arranged on the emission layer 220.

The capping layer 300 includes an organic compound represented by Formula 1, which will be described below.

The hole transporting region 210-215 is provided on the first electrode 110. The hole transporting region 210-215 may include a hole injection layer 210, a hole transporting layer 215, a hole buffer layer and/or an electron blocking layer (EBL). The hole transporting region 210-215 serves to ensure smooth hole injection and transport into the emission layer. The hole transporting region 210-215 is generally larger in thickness than the electron transporting region because the hole mobility is larger than the electron mobility.

The hole transporting region 210-215 may have a monolayer structure composed of a single material, a monolayer structure composed of different materials or a multilayer structure consisting of a plurality of layers composed of different materials.

For example, the hole transporting region 210-215 may include a hole injection layer 210 and/or a hole transporting layer 215. Alternatively, the hole transporting region 210-215 may have a monolayer structure composed of a hole injection material and a hole transporting material. Alternatively, the hole transporting region 210-215 may have a monolayer structure composed of a plurality of different materials. Alternatively, the hole transporting region 210-215 may have a multilayer structure consisting of a hole injection layer 210 and a hole transporting layer 215 sequentially stacked on the first electrode 110. Alternatively, the hole transporting region 210-215 may have a multilayer structure consisting of a hole injection layer 210, a hole transporting layer 215, and a hole buffer layer sequentially stacked on the first electrode 110. Alternatively, the hole transporting region 210-215 may have a multilayer structure consisting of a hole injection layer 210, a hole buffer layer, a hole transporting layer 215, and a hole buffer layer sequentially stacked on the first electrode 110. Alternatively, the hole transporting region 210-215 may have a multilayer structure consisting of a hole injection layer 210, a hole transporting layer 215, and an electron blocking layer (EBL) sequentially stacked on the first electrode 110. However, the hole transporting region is not limited to the above structures.

The hole injection layer 210 of the hole transporting region 210-215 may be formed on the anode by any suitable method such as vacuum deposition, spin coating, casting or LB deposition. For example, vacuum deposition for the formation of the hole injection layer 210 may be performed at a rate of about 1 Å/s at 100 to 500° C. The vacuum deposition conditions are not particularly limited and can be freely controlled depending on the kind of a material for the hole injection layer 210 and the desired structure and thermal properties of the hole injection layer 210. Alternatively, the hole injection layer 210 may be formed by spin coating. The coating conditions may vary depending on the kind of a material for the hole injection layer 210 and the characteristics of layers forming interfaces with the hole injection layer 210. An appropriate coating speed and a suitable thermal process for solvent removal after coating are required to make the hole injection layer 210 even.

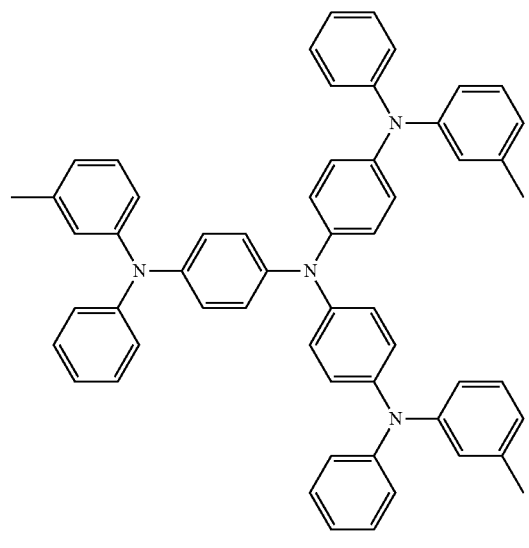

m-MTDATA

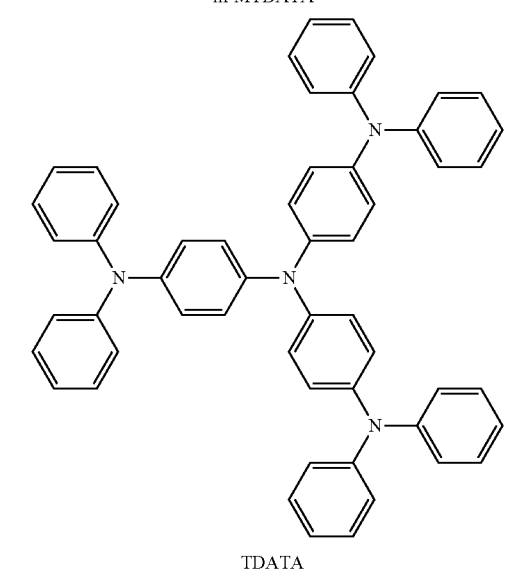

TDATA

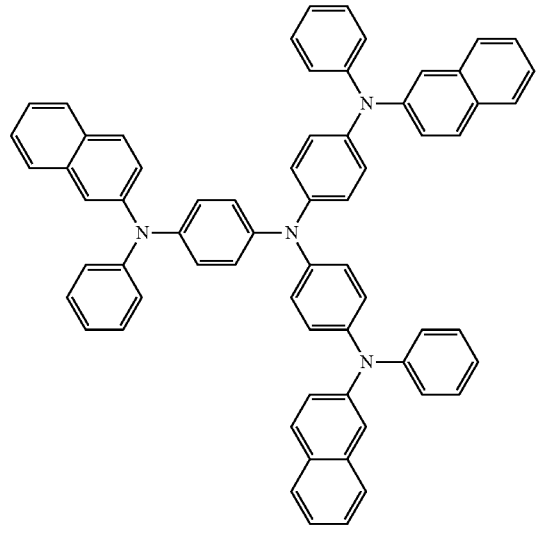

2-TNATA

For example, the hole transporting region 210-215 may include one or more of m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and polyaniline/poly(4-styrenesulfonate) (Pani/PSS).

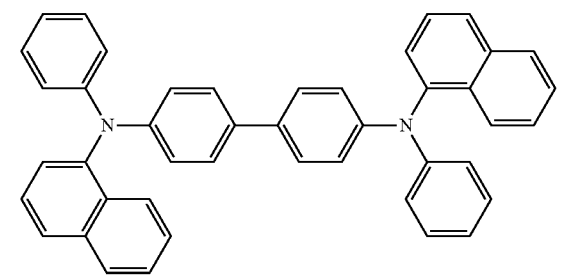

NPB

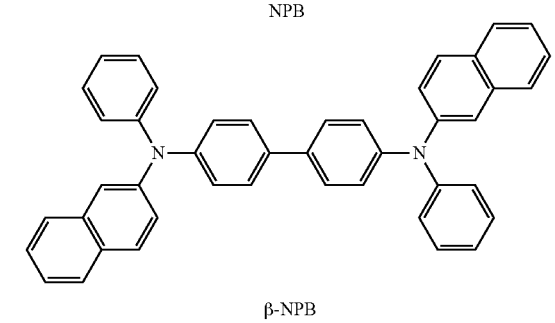

β-NPB

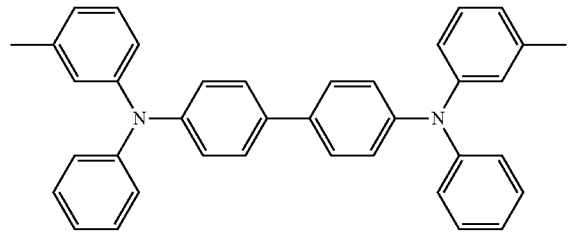

TPD

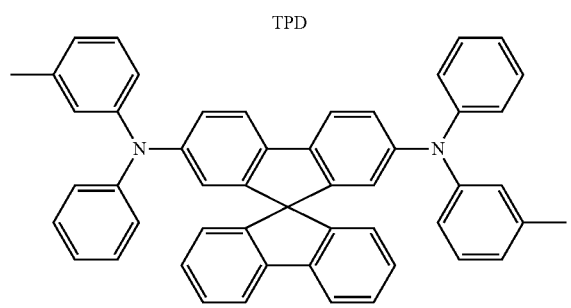

Spiro-TPD

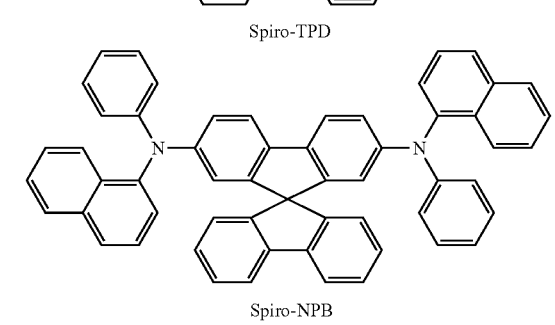

Spiro-NPB

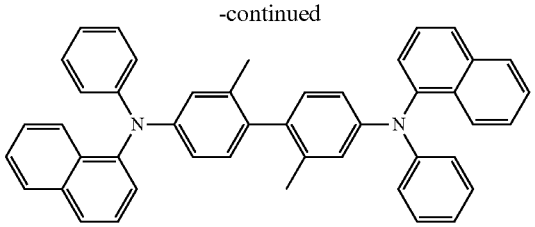

methylated-NPB

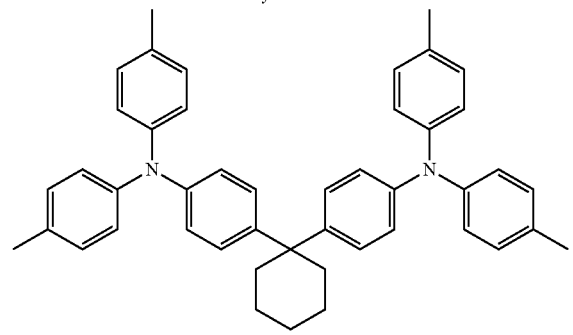

TAPC

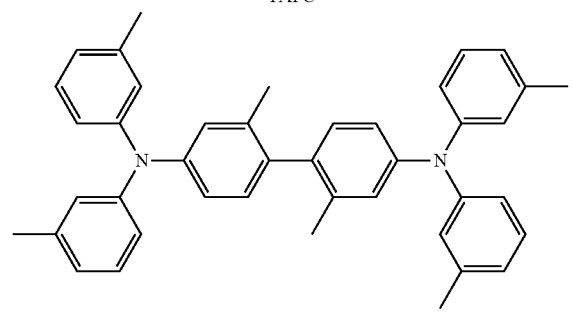

HMTPD

The hole transporting region 210-215 may have a thickness of 100 to 10,000 Å and the constituent organic layers of the hole transporting region 210-215 do not need to have the same thickness. For example, the hole injection layer 210 may have a thickness of 50 Å, the hole transporting layer 215 may have a thickness of 1000 Å, and the electron blocking layer may have a thickness of 500 Å. The thickness of the hole transporting region 210-215 can be determined to such a degree that the efficiency and lifetime of the organic electroluminescent device are satisfactory without an excessive increase in the driving voltage of the organic electroluminescent device.

The organic layer 200 may include one or more layers selected from the group consisting of a hole injection layer 210, a hole transporting layer 215, a functional layer having functions of injecting and transporting holes, a buffer layer, an electron blocking layer, an emission layer 220, a hole blocking layer, an electron transporting layer 230, an electron injection layer 235, and a functional layer having functions of transporting and injecting electrons.

The hole transporting region 210-215 may be doped with a charge generating material to improve the characteristics (e.g., electrical properties) of the organic electroluminescent device, like the emission layer 220. This doping into the hole transporting region 210-215 can improve the electrical properties of the organic electroluminescent device.

The charge generating material is generally a material with very low HOMO and LUMO energy levels. For example, the LUMO energy level of the charge generating material is similar to the HOMO energy level of a material for the hole transporting layer 215. The low LUMO energy level facilitates hole transfer to the adjacent hole transporting layer 215 based on the electron vacancy in the LUMO, achieving improved electrical properties.

The charge generating material may be, for example, a p-type dopant. Non-limiting examples of such p-type dopants include: quinone derivatives such as tetracyanoquinodimethane (TCNQ) and 2,3,5,6-tetrafluoro-tetracyano-1,4-benzoquinodimethane (F4-TCNQ); metal oxides such as tungsten oxides and molybdenum oxides; and cyano group-containing compounds.

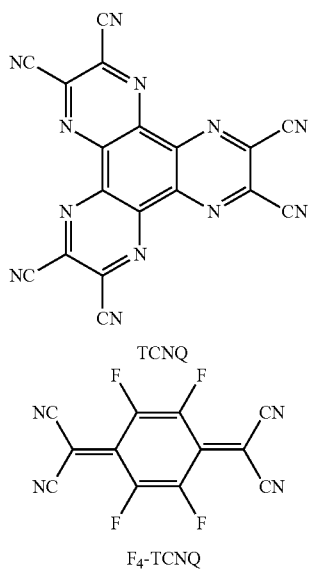

The hole transporting region 210-215 may further include a charge generating material to achieve improved conductivity, in addition to the aforementioned materials.

The charge generating material may be uniformly or non-uniformly dispersed in the hole transporting region 210-215. The charge generating material may be, for example, a p-type dopant. Non-limiting examples of such p-type dopants include: quinone derivatives such as tetracyanoquinodimethane (TCNQ) and 2,3,5,6-tetrafluoro-tetracyano-1,4-benzoquinodimethane (F4-TCNQ); metal oxides such as tungsten oxides and molybdenum oxides; and cyano group-containing compounds.

As described above, the hole transporting region 210-215 may further include a hole buffer layer and/or an electron blocking layer, in addition to the hole injection layer 210 and the hole transporting layer 215. The hole buffer layer may compensate for a resonance distance of light emitted from the emission layer 220 depending on the wavelength of the light to enhance the efficiency of light emission. The hole buffer layer may include the same material as the hole transporting region 210-215.

The electron blocking layer serves to prevent the injection of electrons from the electron transporting region 230-235 into the hole transporting region 210-215. The electron blocking layer may be formed using a material having a high T1 value that can not only block the migration of electrons to the hole transporting region but also can prevent excitons formed in the emission layer 220 from diffusing into the hole transporting region 210-215. For example, a host with a high T1 value for the emission layer 220 is usually used as a material for the electron blocking layer.

The emission layer 220 is provided on the hole transporting region 210-215. For example, the emission layer 220 may have a thickness of 100 Å to 1000 Å or 100 Å to 300 Å. The emission layer 220 may have a monolayer structure composed of a single material, a monolayer structure composed of different materials or a multilayer structure consisting of a plurality of layers composed of different materials.

The emission layer 220 is a region where holes recombine with electrons to form excitons. Materials for the emission layer 220 should have appropriate energy band gaps such that excellent luminescent properties are obtained and a desired color of light is emitted. The materials for the emission layer 220 are typically a host and a dopant but are not limited thereto.

The host may include at least one of TPBi, TBADN, ADN (also called "DNA"), CBP, CDBP, TCP, and mCP but is not limited thereto.

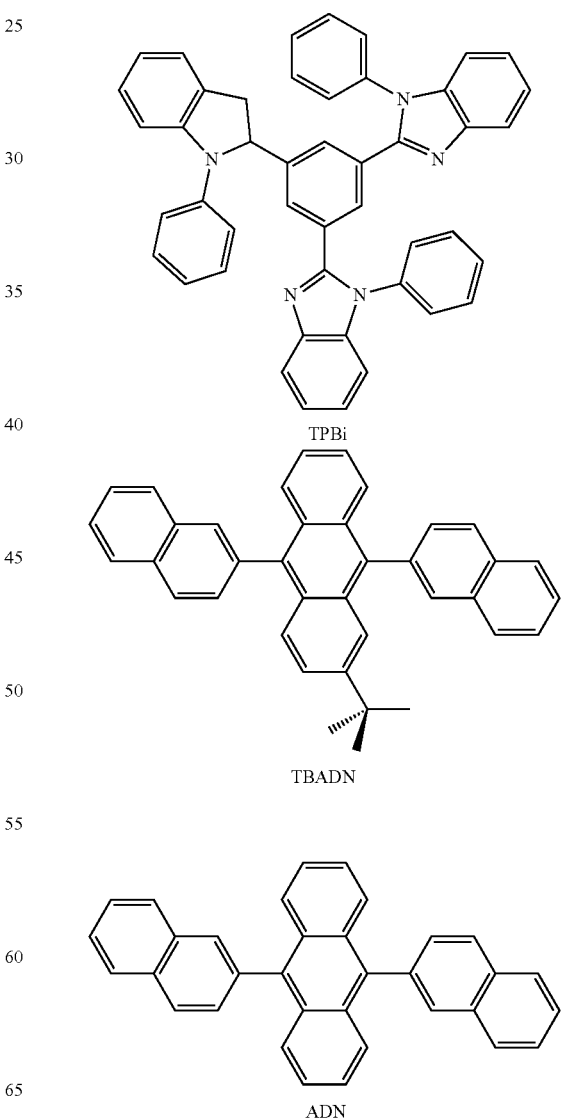

-continued

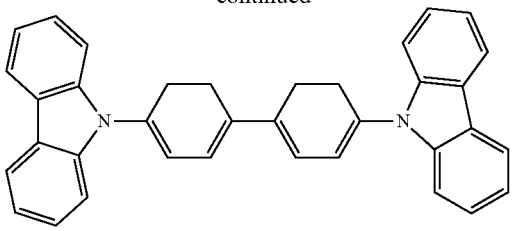

CBP

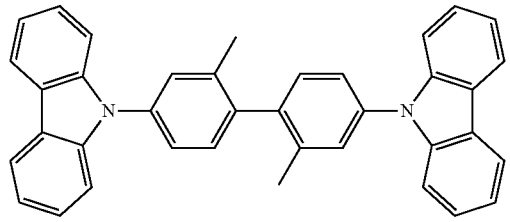

CDBP

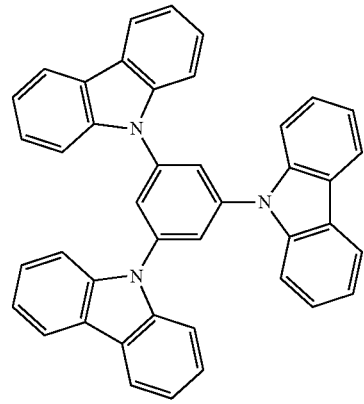

TCP

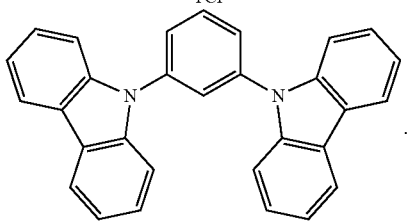

mCP

In one embodiment, the dopant may be an organometallic complex. The content of the dopant may generally be selected from 0.01 to 20% but is not limited thereto. The electron transporting region 230-235 is provided on the emission layer 220.

The electron transporting region 230-235 may include a hole blocking layer, an electron transporting layer 230, and/or an electron injection layer 235 but is not limited thereto.

The electron transporting region 230-235 may have a monolayer structure composed of a single material, a monolayer structure composed of different materials or a multilayer structure consisting of a plurality of layers composed of different materials.

For example, the electron transporting region 230-235 may include an electron injection layer 235 and/or an electron transporting layer 230. Alternatively, the electron transporting region 230-235 may have a monolayer structure composed of an electron injection material and an electron transporting material. Alternatively, the electron transporting region 230-235 may have a monolayer structure composed of a plurality of different materials. Alternatively, the electron transporting region 230-235 may have a multilayer structure consisting of an electron transporting layer 230 and an electron injection layer 235 sequentially stacked on the emission layer 220. Alternatively, the electron transporting region 230-235 may have a multilayer structure consisting of a hole blocking layer, an electron transporting layer 230, and an electron injection layer 235 sequentially stacked on the emission electrode 220. However, the electron transporting region is not limited to the above structures. The thickness of the electron transporting region 230-235 may be, for example, 1000 Å to 1500 Å.

The electron transporting region 230-235 may be formed by any suitable method such as vacuum deposition, spin coating, casting, Langmuir-Blodgett (LB) deposition, inkjet printing, laser printing or laser induced thermal imaging (LITI).

The electron transporting layer 230 of the electron transporting region 230-235 may include an anthracene-based compound. Non-limiting examples of suitable materials for the electron transporting layer 230 include, but are not limited to, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-ylphenyl)-9,10-dinaphthylanthracene, 1,3,5-tri(1-phenyl-1H-benzo[d]imidazol-2-yl)phenyl) (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), beryllium bis(benzoquinolin-10-olate) (Bebq2), 9,10-di(naphthalene-2-yl)anthracene (ADN). These materials may be used alone or as a mixture thereof

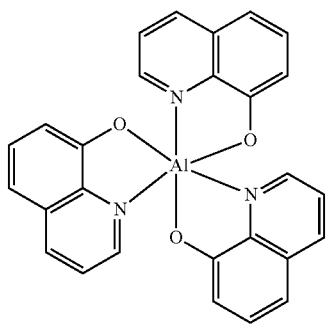

Alq3

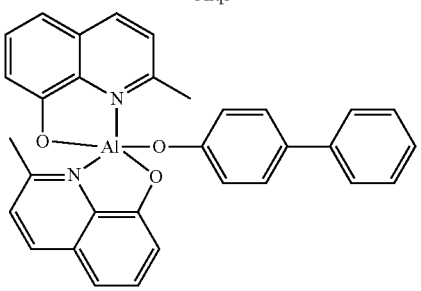

BAlq

-continued

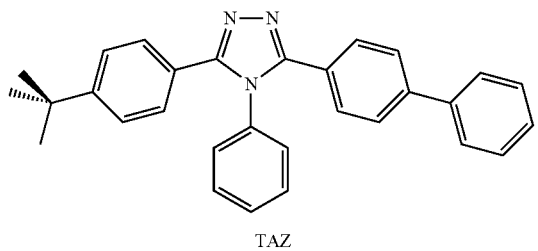

TAZ

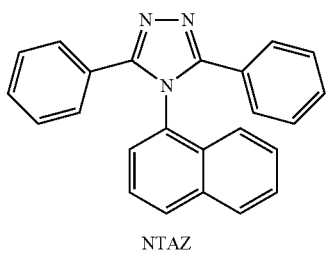

NTAZ

The material for the electron transporting layer 230 may be selected from materials with either high or low electron mobility. The selection varies depending on the structure of the organic electroluminescent device. The electron transporting layer 230 may be optionally doped with Liq or Li.

The thickness of the electron transporting layer 230 may be, for example, in the range of 100 Å to 1000 Å, for example, 150 Å to 500 Å. Within this range, satisfactory electron transporting properties can be obtained without a substantial increase in driving voltage.

The electron injection layer 235 of the electron transporting region 230-235 may include a metal material that facilitates electron injection. Examples of suitable metal materials for the electron injection layer 235 include, but are not limited to, LiF, lithium quinolate (LiQ), $Li_2O$, BaO, NaCl, CsF, lanthanide metals such as Yb, and metal halides such as RbCl and RbI.

The electron injection layer 235 may be formed of a mixture of an electron transporting material and an insulating organometallic salt. The organometallic salt may be a material having an energy band gap of approximately 4 eV or more. Specific examples of suitable organometallic salts for the electron injection layer include metal acetates, metal benzoates, metal acetoacetates, metal acetylacetonates, and metal stearates. The thickness of the electron injection layer 235 is in the range of 1 Å to 100 Å, preferably 3 Å to 90 Å. Within this range, satisfactory electron injection properties can be obtained without a substantial increase in driving voltage.

As mentioned previously, the electron transporting region 230-235 may include a hole blocking layer. For example, the hole blocking layer may include at least of 2,9-dimethyl-4, 7-diphenyl-1,10-phenanthroline (BCP), 4,7-diphenyl-1,10-phenanthroline (Bphen), and Balq. However, the material for the hole blocking layer is not limited.

The second electrode 120 is provided on the electron transporting region 230-235. The second electrode 120 may be a common electrode or a cathode. The second electrode 120 may be a transmissive or transflective electrode. Unlike the first electrode 110, the second electrode 120 may be made of a combination of a relatively low work function metal, an electrically conductive compound, an alloy, etc.

The second electrode 120 is a transflective or reflective electrode. The second electrode 120 may include lithium (Li), magnesium (Mg), aluminum (Al), aluminum-lithium (Al—Li), calcium (Ca), magnesium-indium (Mg—In), magnesium-silver (Mg—Ag), or a compound or mixture containing the metal or alloy (e.g., a mixture of Ag and Mg). Alternatively, the second electrode 120 may have a multi-layer structure consisting of a reflective or transflective film and a transparent conductive film. The material for the reflective or transflective film is the same as that described above for the transflective or reflective electrode. For example, the transparent conductive film may be formed of indium tin oxide (ITO), indium zinc oxide (IZO), zinc oxide (ZnO) or indium tin zinc oxide (ITZO).

Although not shown, the second electrode 120 may be connected to an auxiliary electrode. This connection can reduce the resistance of the second electrode 120.

The substrate 100 on which the electrodes and the organic layer are disposed may be made of a rigid or flexible material. For example, the rigid material may be soda-lime glass, alkali-free glass or aluminosilicate glass and the flexible material may be polycarbonate (PC), polyethersulfone (PES), a cyclic olefin copolymer (CEC), polyethylene terephthalate (PET) or polyethylene naphthalate (PEN).

When a voltage is applied to the first and second electrodes 110 and 120 of the organic electroluminescent device, holes are injected from the first electrode 110 and migrate to the emission layer 220 through the hole transporting region 210-215 and electrons are injected from the second electrode 120 and migrate to the emission layer 220 through the electron transporting region 230-235. The electrons recombine with the holes in the emission layer 220 to form excitons, which fall from the excited state to the ground state to emit light.

The path of light generated in the emission layer 220 tends to vary depending on the refractive indices of the organic/inorganic materials constituting the organic electroluminescent device. Only rays of light incident on the second electrode 120 at angles smaller than the critical angle of the second electrode 120 can pass through the second electrode 120. Rays of light coming into contact with the second electrode 120 at angles larger than the critical angle of the second electrode 120 are totally reflected, and as a result, they cannot be emitted outside the organic electroluminescent device.

Haze may be caused by the orientation of the organic material used in the capping layer 300 in the form of a thin film. The occurrence of haze causes scattering of light at a specific wavelength to prevent the light from emitting to the outside, leading to a considerable reduction in the efficiency of the organic electroluminescent device.

Substitution of the phenylene moieties between the tertiary amine and the benzazole groups in Formula 1 with various alkyl groups affects the orientation of the organic material used in the capping layer 300 in the form of a thin film and the roughness of the capping layer 300, causing haze in the organic electroluminescent device.

The compound of Formula 1 that is unsubstituted with alkyl does not cause haze, resulting in an increase in the luminescent efficiency of the organic electroluminescent device.

A high refractive index of the capping layer 300 reduces the total reflection of light entering the capping layer 300, contributing to an improvement in luminescent efficiency.

An appropriate thickness of the capping layer 300 maximizes the number of micro-cavities, contributing to high efficiency and improved color purity.

The capping layer 300 is placed at the outermost position of the organic electroluminescent device and has a great influence on the characteristics of the device without affecting the driving of the device at all. Therefore, the capping layer 300 is important from both viewpoints of protecting the inside of the organic electroluminescent device and improving the characteristics of the device. The organic materials absorb light energy in specific wavelength ranges depending on their energy band gaps. When the energy band gaps are adjusted such that light in the UV region capable of affecting the organic materials present in the organic electroluminescent device is absorbed, the capping layer 300 containing the organic materials can be used to improve the optical properties of the organic electroluminescent device while protecting the organic electroluminescent device.

A description will be given of the tribenzazole amine derivative used in the organic layer and/or the capping layer.

The tribenzazole amine derivative of the present invention is represented by Formula 1:

[Formula 1]

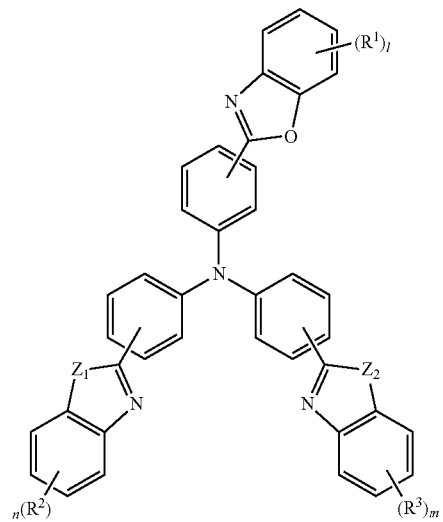

wherein $Z_1$ and $Z_2$ are each independently O or S, $R^1$, $R^2$, and $R^3$ are identical to or different from each other and are each independently hydrogen, deuterium, substituted or unsubstituted alkyl, substituted or unsubstituted cycloalkyl, substituted or unsubstituted alkoxy, substituted or unsubstituted aryloxy, substituted or unsubstituted aralkyl, substituted or unsubstituted alkylaryl, substituted or unsubstituted allyl or substituted or unsubstituted heteroaryl, and l, n, and m are integers from 0 to 4.

The tribenzazole amine derivative represented by Formula 1 may be selected from, but not limited to, the compounds represented by the following formulae:

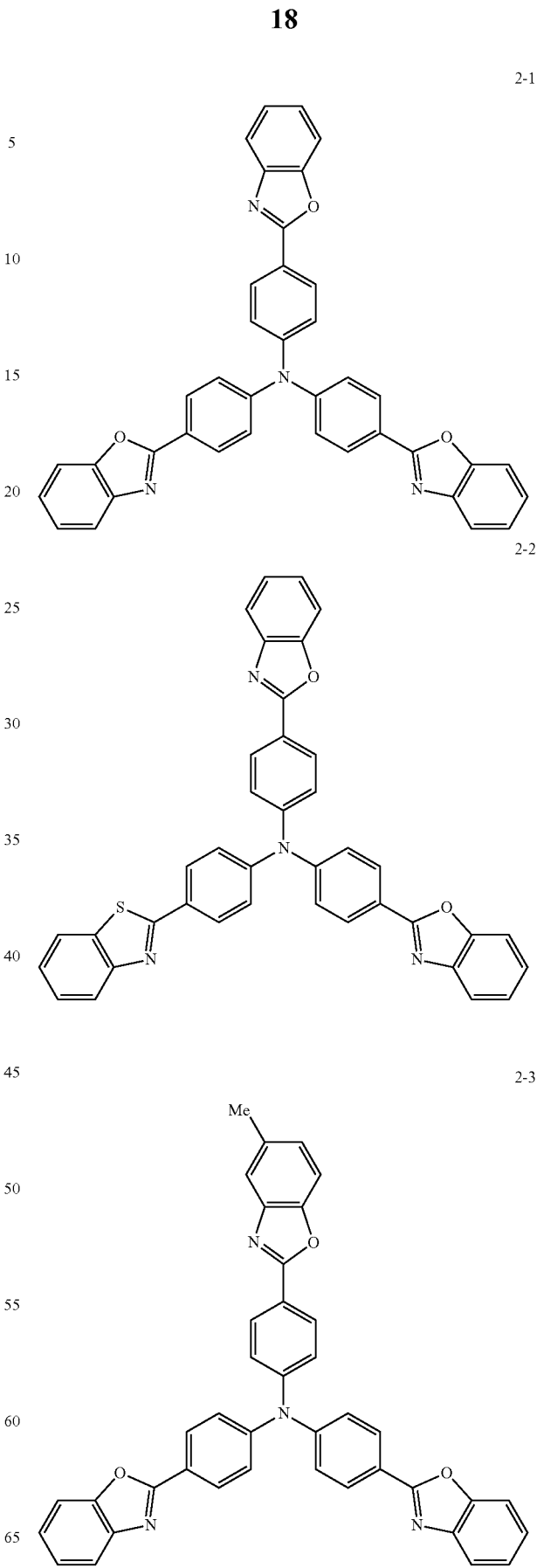

2-4
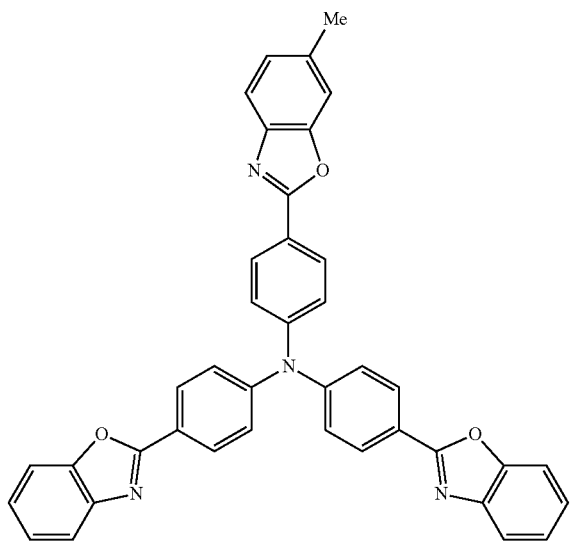
2-5
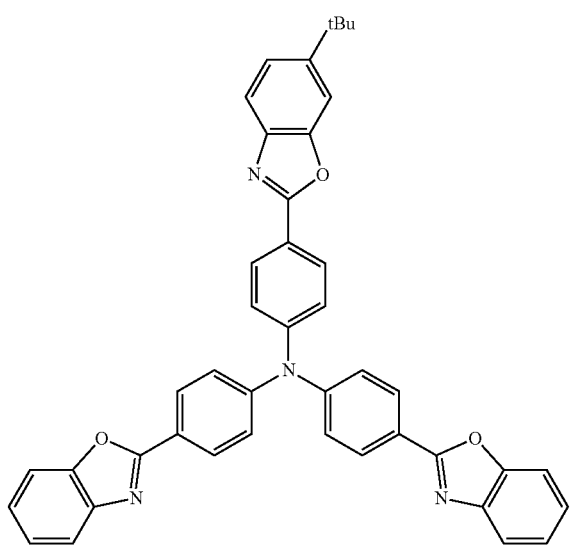
2-6
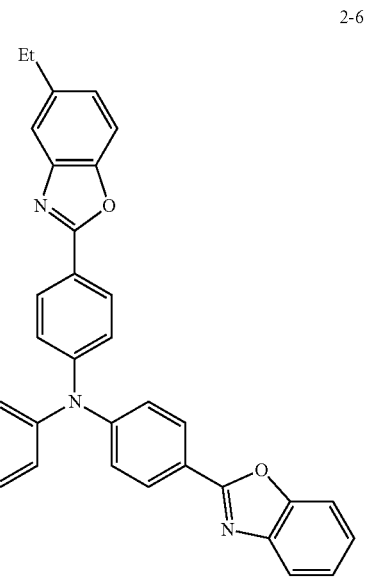
2-7
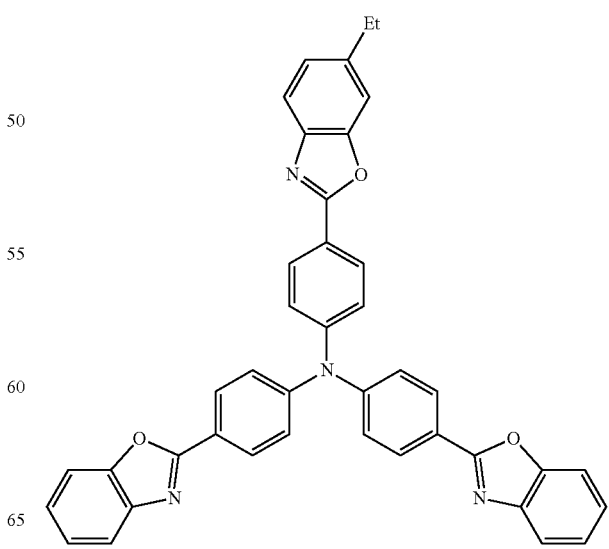

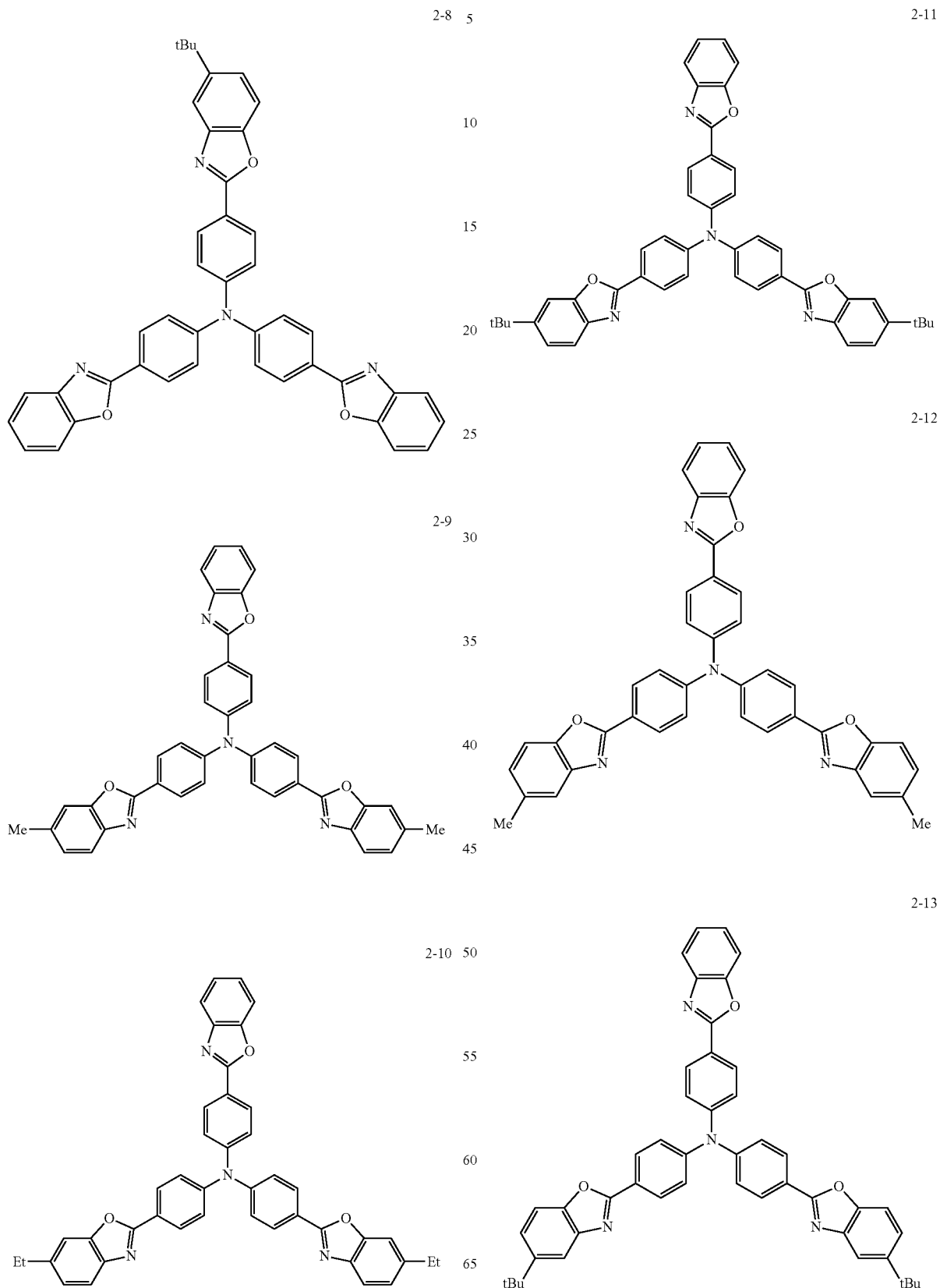

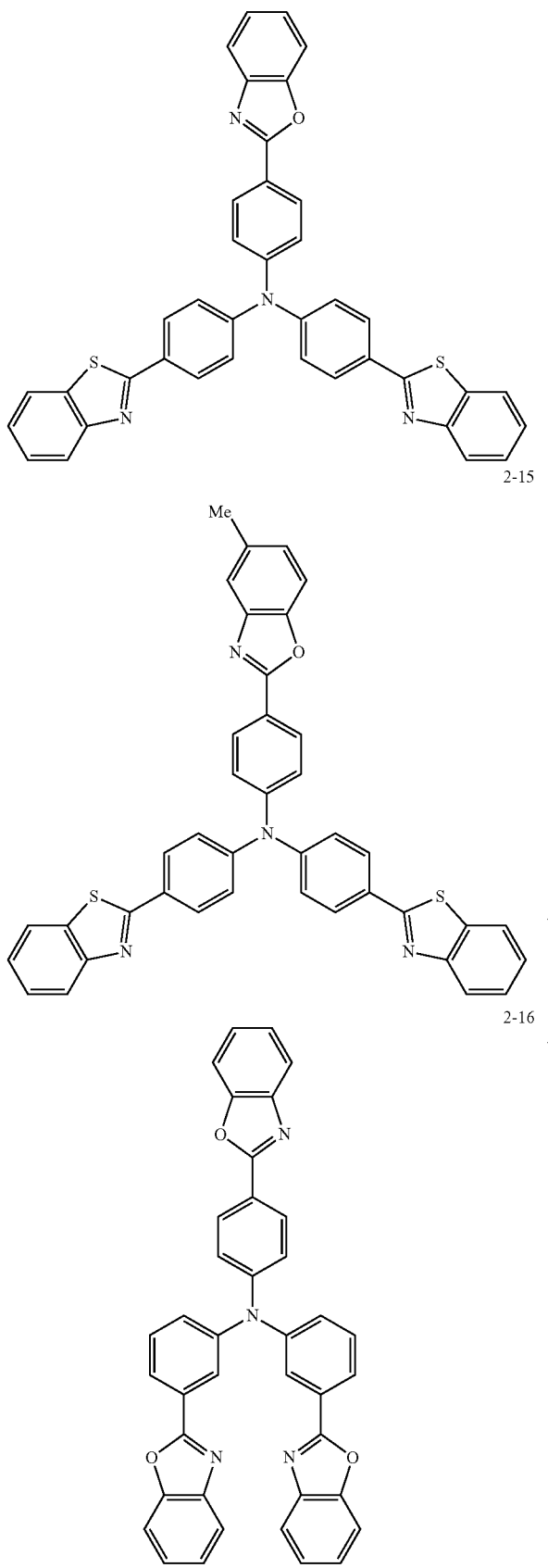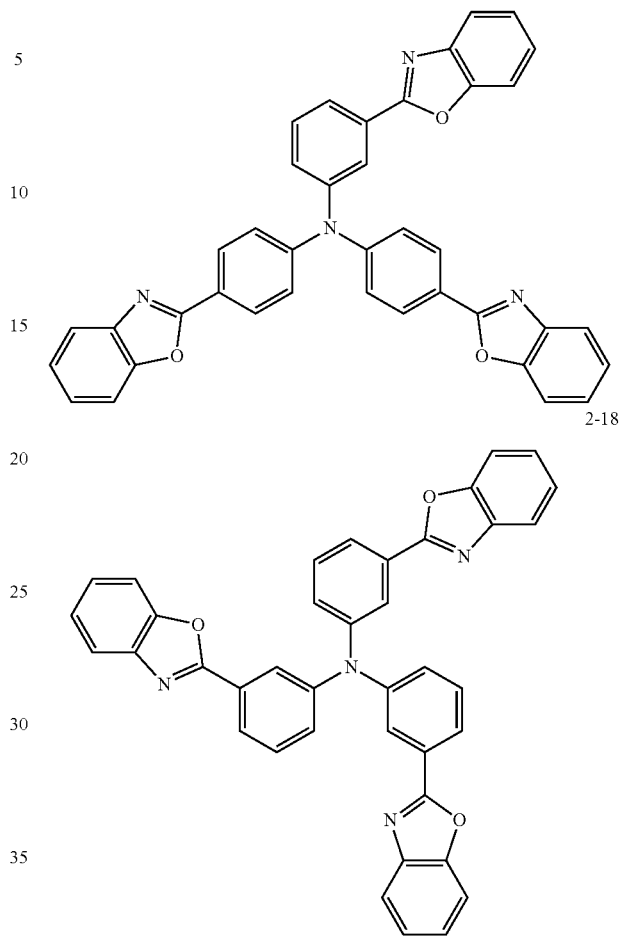

MODE FOR CARRYING OUT THE INVENTION

Organic electroluminescent devices and tribenzazole amine derivatives according to exemplary embodiments of the present invention will be specifically explained with reference to the following examples, including comparative examples. However, these examples are merely illustrative to assist in understanding the present invention and the scope of the present invention is not limited thereto.

EXAMPLES

Synthesis Example 1: Synthesis of Intermediate 3

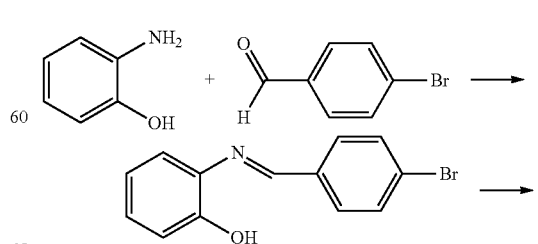

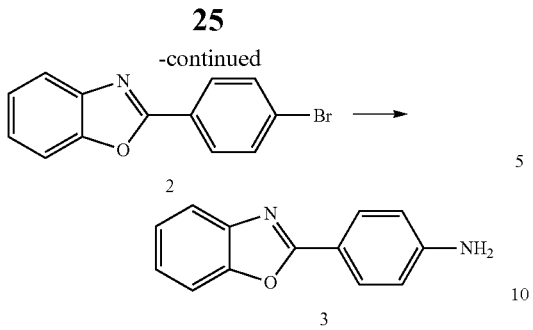
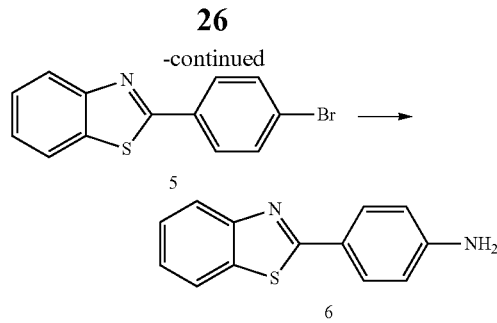

Synthesis of Intermediate 2

10.0 g (0.09 mol) of 2-aminophenol, 16.9 g (0.09 mol) of 4-bromobenzaldehyde, and 114 mL of ethanol were stirred at room temperature for 6 h. After completion of the reaction, the solvent was distilled off under reduced pressure, followed by drying to afford crude Intermediate 1. Intermediate 1 was used for the subsequent reaction without further purification.

Intermediate 1 was dissolved in 370 mL of dichloromethane, and then 22.8 g (0.10 mol) of 2,3-dichloro-5,6-dicyano-p-benzoquinone (DDQ) was slowly added thereto with stirring at room temperature. After stirring for one day, the reaction mixture was purified by column chromatography (DCM) and solidified with methanol to afford 30.5 g (yield 94.4%) of Intermediate 2 as a white solid.

Synthesis of Intermediate 3

10.0 g (36.50 mmol) of Intermediate 2, 7.9 g (43.80 mmol) of benzophenone imine, and 243 mL of toluene were placed in a 1000 mL one-neck flask, and then 1.1 g (1.82 mmol) of Pd(dba)$_2$, 2.3 g (3.65 mmol) of BINAP, and 35.7 g (109.40 mmol) of Cs$_2$CO$_3$ were added thereto. The mixture was stirred at 110° C. all day. After completion of the reaction, the reaction mixture was cooled to room temperature, filtered through a pad of celite using chloroform under reduced pressure, and distilled under reduced pressure to remove the solvent. The resulting residue was diluted with 182 mL of THF and acidified to pH<2 by slow addition of 30 mL of concentrated hydrochloric acid. The mixture was stirred at room temperature all day to precipitate a solid. The solid was collected by filtration, washed with chloroform, adjusted to a basic pH (pH>8) with a saturated Na$_2$CO$_3$ solution, extracted with chloroform, dried over MgSO$_4$, distilled under reduced pressure to remove the solvent, and slurried with DCM and hexane to afford 5.9 g (yield 78.2%) of Intermediate 3 as a yellow solid.

Synthesis Example 2: Synthesis of Intermediate 6

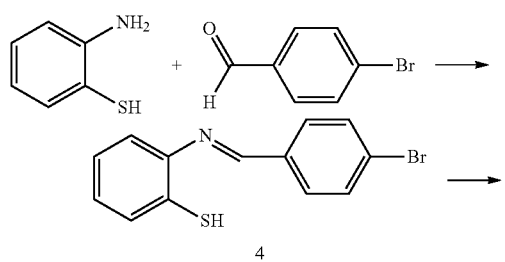

Synthesis of Intermediate 5

10.0 g (76.88 mmol) of 2-aminobenzothiol, 12.8 g (69.42 mol) of 4-bromobenzaldehyde, and 130 mL of ethanol were stirred at room temperature for 6 h. After completion of the reaction, the solvent was distilled off under reduced pressure, followed by drying to afford crude Intermediate 4. Intermediate 4 was used for the subsequent reaction without further purification.

Intermediate 4 was dissolved in 320 mL of dichloromethane, and then 19.9 g (0.09 mol) of 2,3-dichloro-5,6-dicyano-p-benzoquinone (DDQ) was slowly added thereto with stirring at room temperature. After stirring for one day, the reaction mixture was purified by column chromatography (DCM) and solidified with methanol to afford 26.6 g (yield 90.2%) of Intermediate 5 as a white solid.

Synthesis of Intermediate 6

26.6 g (91.67 mmol) of Intermediate 5, 19.9 g (110.00 mmol) of benzophenone imine, and 270 mL of toluene were placed in a 1000 mL one-neck flask, and then 2.6 g (4.58 mmol) of Pd(dba)$_2$, 5.7 g (9.17 mmol) of BINAP, and 89.6 g (275.00 mmol) of Cs$_2$CO$_3$ were added thereto. The mixture was stirred at 110° C. all day. After completion of the reaction, the reaction mixture was cooled to room temperature, filtered through a pad of celite using chloroform under reduced pressure, and distilled under reduced pressure to remove the solvent. The resulting mixture was diluted with 300 mL of THF and acidified to pH<2 by slow addition of 30 mL of concentrated hydrochloric acid. The mixture was stirred at room temperature all day to precipitate a solid. The solid was collected by filtration, washed with chloroform, adjusted to a basic pH (pH>8) with a saturated Na$_2$CO$_3$ solution, extracted with chloroform, dried over MgSO$_4$, distilled under reduced pressure to remove the solvent, and slurried with DCM and hexane to afford 17.8 g (yield 85.8%) of Intermediate 6 as a yellow solid.

Synthesis Example 3: Synthesis of Intermediate 9

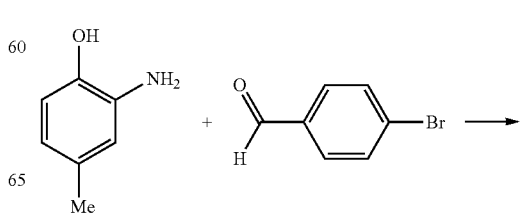

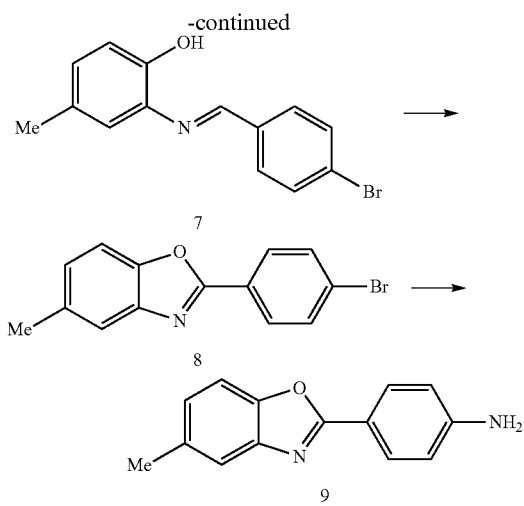

Synthesis of Intermediate 8

25.0 g (203.00 mmol) of 2-amino-4-methylphenol, 45.1 g (243.60 mmol) of 4-bromobenzaldehyde, and 812 mL of ethanol were stirred in a 2000 mL one-neck flask at 80° C. for 3 h. After completion of the reaction, the reaction mixture was cooled to room temperature and distilled under reduced pressure to remove the solvent. The precipitated solid was dried under vacuum for 4 h to afford 58.9 g of Intermediate 7 as a brown solid. Intermediate 4 was used for the subsequent reaction without further purification.

58.9 g (202.90 mmol) of Intermediate 7 and 1015 mL of dichloromethane were stirred in a 2000 mL one-neck flask at room temperature.

To the mixture was slowly added 55.3 g (243.60 mmol) of 2,3-dichloro-5,6-dicyano-p-benzoquinone (DDQ) at room temperature. The resulting mixture was stirred all day. After completion of the reaction, the reaction mixture was filtered through a pad of celite using DCM and distilled under reduced pressure to remove the solvent. The resulting mixture was purified by SiO$_2$ column chromatography (DCM:EA:HEX=1:1:3) and slurried with DCM and MeOH to afford 49.58 g (yield 84.8%, purity 99.6%) of Intermediate 8 as a beige solid.

Synthesis of Intermediate 9

10.0 g (34.70 mmol) of Intermediate 8, 7.6 g (41.60 mmol) of benzophenone imine, and 174 mL of toluene were placed in a 500 mL one-neck flask, and then 1.0 g (1.73 mmol) of Pd(dba)$_2$, 2.2 g (3.47 mmol) of BINAP, and 10.0 g (104.20 mmol) of sodium tert-butoxide were added thereto. The mixture was stirred at 110° C. for 3 h. After completion of the reaction, the reaction mixture was cooled to room temperature, filtered through a pad of celite using chloroform, and distilled under reduced pressure to remove the solvent. The resulting mixture was diluted with 174 mL of THF and acidified to pH<2 by slow addition of 174 mL of 6 N HCl. After stirring at room temperature all day, the reaction mixture was adjusted to a basic pH (pH>8) with a saturated Na$_2$CO$_3$ solution, extracted with EA, dried over MgSO$_4$, distilled under reduced pressure to remove the solvent, purified by SiO$_2$ column chromatography (EA:HEX=1:2), and slurried with acetone and hexane to remove impurities, affording 3.4 g (yield 44.8%) of Intermediate 9 as a beige solid.

Synthesis Example 4: Synthesis of Intermediate 12

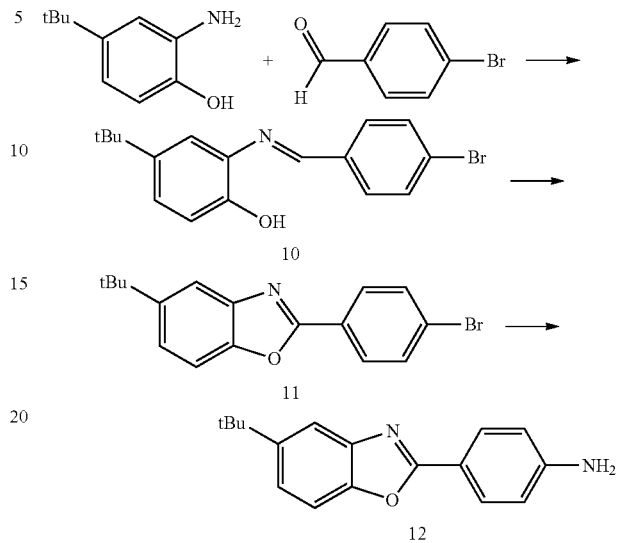

Synthesis of Intermediate 11

10.0 g (60.52 mmol) of 2-amino-4-t-butylphenol, 11.2 g (60.52 mmol) of 4-bromobenzaldehyde, and 100 mL of ethanol were stirred at room temperature for 6 h. After completion of the reaction, the solvent was distilled off under reduced pressure, followed by drying to afford crude Intermediate 10. Intermediate 10 was used for the subsequent reaction without further purification.

Intermediate 10 was dissolved in 370 mL of dichloromethane, and then 15.1 g (66.57 mmol) of 2,3-dichloro-5,6-dicyano-p-benzoquinone (DDQ) was slowly added thereto with stirring at room temperature. After stirring for one day, the reaction mixture was purified by column chromatography (DCM) and solidified with methanol to afford 15.3 g (yield 76.5%) of Intermediate 11 as a white solid.

Synthesis of Intermediate 12

5.0 g (15.14 mmol) of Intermediate 11, 4.1 g (22.71 mmol) of benzophenone imine, 870.0 mg (1.51 mmol) of Pd(dba)$_2$, 1.9 g (3.03 mmol) of BINAP, 14.8 g (45.42 mmol) of Cs$_2$CO$_3$, and 70 mL of toluene were placed in a 250 mL one-neck flask. The mixture was stirred at 110° C. for 12 h. After completion of the reaction, the reaction mixture was cooled to room temperature, filtered through a pad of celite, distilled under reduced pressure, and added with 70 mL of THF and 20 mL of concentrated HCl. The mixture was stirred for one day. The precipitated solid was collected by filtration, washed with chloroform, neutralized with a Na$_2$CO$_3$ solution, and extracted with chloroform. The organic layer was concentrated and solidified with hexane to afford 2.0 g (yield 50.3%) of Intermediate 12 as a white solid.

Synthesis Example 5: Synthesis of Intermediate 15

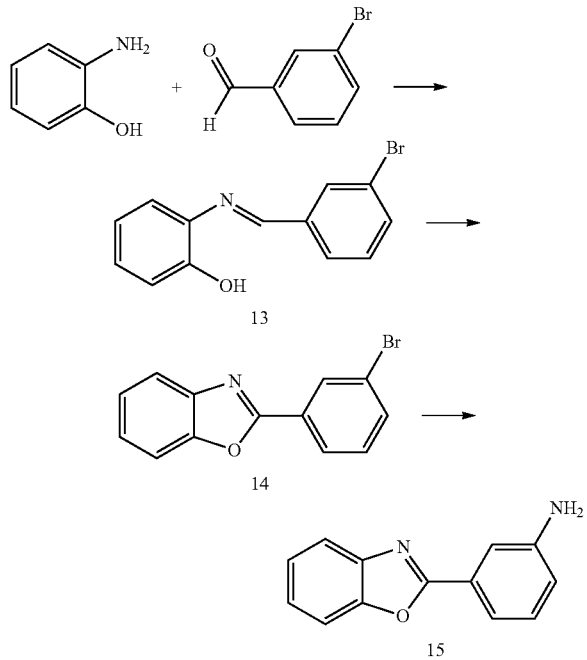

Synthesis Example 6: Synthesis of Intermediate 18

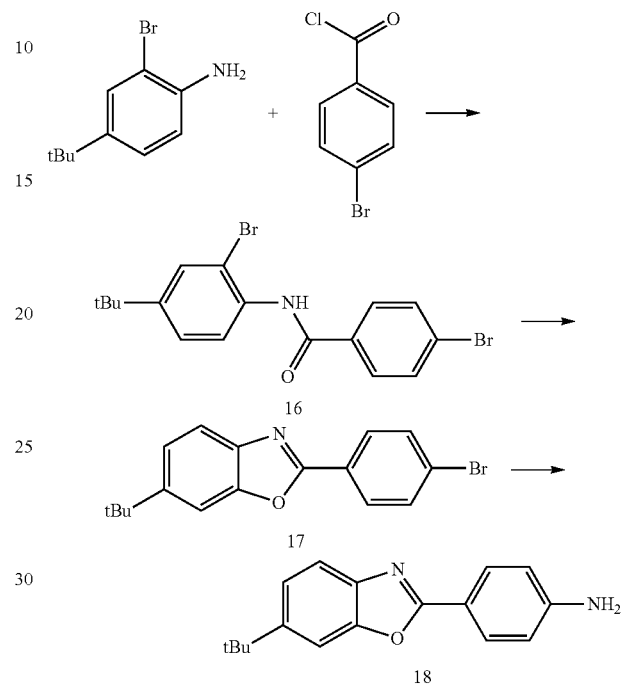

Synthesis of Intermediate 14

10.0 g (0.09 mol) of 2-aminophenol, 16.9 g (0.09 mol) of 4-bromobenzaldehyde, and 114 mL of ethanol were stirred at room temperature for 6 h. After completion of the reaction, the solvent was distilled off under reduced pressure, followed by drying to afford crude Intermediate 13. Intermediate 13 was used for the subsequent reaction without further purification.

Intermediate 13 was dissolved in 370 mL of dichloromethane, and then 22.8 g (0.10 mol) of 2,3-dichloro-5,6-dicyano-p-benzoquinone (DDQ) was slowly added thereto with stirring at room temperature. After stirring for one day, the reaction mixture was purified by column chromatography (DCM) and solidified with methanol to afford 30.5 g (yield 94.4%) of Intermediate 14 as a white solid.

Synthesis of Intermediate 15

10.0 g (36.50 mmol) of Intermediate 14, 7.9 g (43.80 mmol) of benzophenone imine, and 243 mL of toluene were placed in a 1000 mL one-neck flask, and then 1.1 g (1.82 mmol) of Pd(dba)$_2$, 2.3 g (3.65 mmol) of BINAP, and 35.7 g (109.40 mmol) of Cs$_2$CO$_3$ were added thereto. The mixture was stirred at 110° C. all day. After completion of the reaction, the reaction mixture was cooled to room temperature, filtered through a pad of celite using chloroform under reduced pressure, and distilled under reduced pressure to remove the solvent. The resulting mixture was diluted with 182 mL of THF and acidified to pH<2 by slow addition of 30 mL of concentrated hydrochloric acid. The mixture was stirred at room temperature all day to precipitate a solid. The solid was collected by filtration, washed with chloroform, adjusted to a basic pH (pH>8) with a saturated Na$_2$CO$_3$ solution, extracted with chloroform, dried over MgSO$_4$, distilled under reduced pressure to remove the solvent, and slurried with DCM and hexane to afford 5.9 g (yield 78.2%) of Intermediate 15 as a yellow solid.

Synthesis of Intermediate 16

30.0 g (157.88 mmol) of 2-bromo-4-tert-butylaniline, 34.6 g (157.88 mmol) of 4-bromobenzoyl chloride, and 300 mL of THF were stirred at room temperature for 3 h. After completion of the reaction, the solvent was distilled off under reduced pressure. The residue was solidified with diisopropyl ether to afford 42.6 g (yield 72.3%) of Intermediate 16 as a white solid.

Synthesis of Intermediate 17

42.6 g (114.20 mmol) of Intermediate 16, 1.1 g (5.71 mmol) of CuI, 2.1 g (11.42 mmol) of 1,10-phenanthroline, 74.4 g (228.41 mmol) of Cs$_2$CO$_3$, and 800 mL of nitrobenzene was stirred under reflux in a 1 L one-neck flask all day. After completion of the reaction, the reaction mixture was filtered through a pad of celite using DCM. After removal of the solvent, the resulting solid was dissolved in chloroform, purified by column chromatography (CHCl$_3$), and solidified with methanol to afford 21.8 g (yield 65.3%) of Intermediate 17 as a light yellow solid.

Synthesis of Intermediate 18

5.0 g (15.14 mmol) of Intermediate 17, 4.1 g (22.71 mmol) of benzophenone imine, 871.0 mg (1.51 mmol) of Pd(dba)$_2$, 1.9 g (3.03 mmol) of BINAP, 8.7 g (90.85 mmol) of NaOtBu, and 80 mL of toluene were mixed in a 250 mL one-neck flask. The reaction was allowed to proceed at 100° C. for 2 h. After completion of the reaction, the reaction mixture was cooled to room temperature, filtered through a pad of celite, distilled under reduced pressure, and added with 50 mL of THF and 50 mL of 6 N HCl. The mixture was stirred for one day. The reaction mixture was neutralized with a Na$_2$CO$_3$ solution, extracted with CHCl$_3$, purified by silica gel column chromatography (Hex:EA=6:1), dissolved in DCM, and solidified while slowly adding dropwise hexane to afford 2.4 g (yield 59.8%) of Intermediate 18 as a yellow solid.

These intermediates were used to synthesize various tribenzazole amine derivatives in the following examples.

Example 1: Synthesis of Compound 2-1 (LT18-30-198)

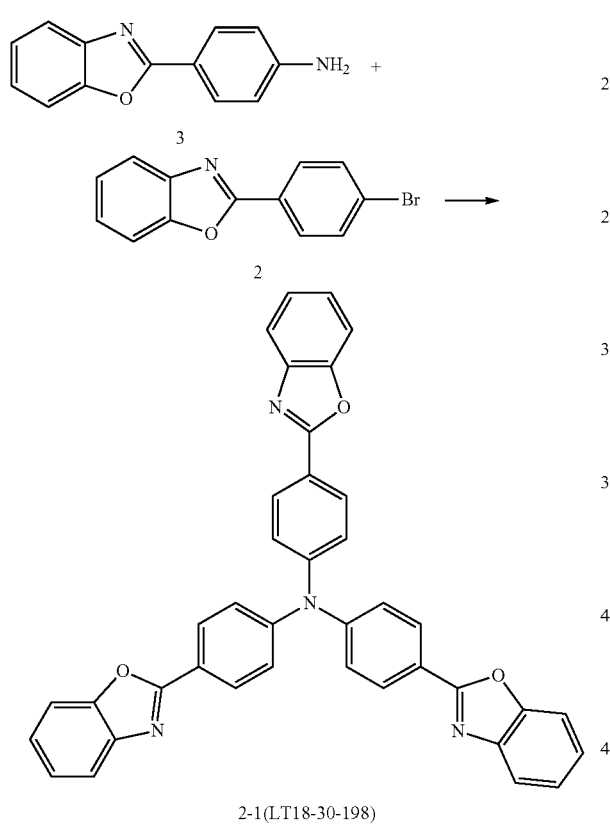

2-1(LT18-30-198)

1.8 g (8.56 mmol) of Intermediate 3, 5.9 g (21.40 mmol) of Intermediate 2, and 85.6 mL of xylene were stirred in a 250 mL one-neck flask at 50° C., and then 0.5 g (0.86 mmol) of Pd(dba)$_2$, 4.9 g (51.40 mmol) of sodium tert-butoxide, and 0.69 g (1.71 mmol) of tri-tert-butylphosphine (50 wt % in toluene) were added thereto. The mixture was allowed to react with stirring at 125-130° C. all day. After completion of the reaction, the reaction mixture was cooled to room temperature, filtered through a pad of celite using CHCl$_3$ under reduced pressure, and distilled under reduced pressure to remove the solvent. The resulting residue was solidified with hexane to precipitate a yellow solid, which was then dissolved in 800 mL of CHCl$_3$ by heating. To the solution was added charcoal. After stirring for 30 min, the reaction mixture was filtered through a pad of celite and SiO$_2$ using a hot mixed solvent (hot CHCl$_3$:EA=20:1) and distilled under reduced pressure to remove the solvent. The resulting residue was purified by SiO$_2$ column chromatography (EA: CHCl$_3$:HEX=1:1:5) and slurried with DCM and hexane to give 3.0 g (yield 59.1%) of Compound 2-1 (LT18-30-198) as a yellow solid.

Example 2: Synthesis of Compound 2-2 (LT18-30-238)

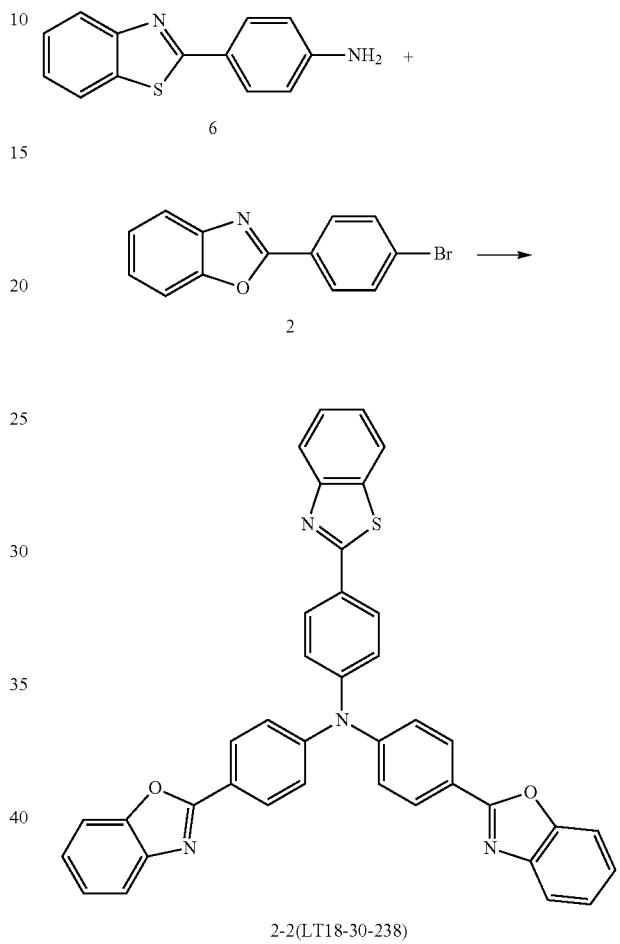

2-2(LT18-30-238)

2.0 g (8.84 mmol) of Intermediate 6, 5.1 g (21.4 mmol) of Intermediate 2, and 100 mL of xylene were stirred in a 250 mL one-neck flask at 50° C., and then 0.5 g (0.88 mmol) of Pd(dba)$_2$, 2.6 g (26.51 mmol) of sodium tert-butoxide, and 0.72 g (1.77 mmol) of tri-tert-butylphosphine (50 wt % in toluene) were added thereto. The mixture was allowed to react with stirring at 125-130° C. all day. After completion of the reaction, the reaction mixture was cooled to room temperature, filtered through a pad of celite using CHCl$_3$ under reduced pressure, and distilled under reduced pressure to remove the solvent. The resulting residue was solidified with hexane to precipitate a yellow solid, which was then dissolved in 800 mL of CHCl$_3$ by heating. To the solution was added charcoal. After stirring for 30 min, the reaction mixture was filtered through a pad of celite and SiO$_2$ using a hot mixed solvent (hot CHCl$_3$:EA=20:1) and distilled under reduced pressure to remove the solvent. The resulting residue was purified by SiO$_2$ column chromatography (EA: CHCl$_3$:HEX=1:1:5) and slurried with DCM and hexane to give 2.6 g (yield 48.0%) of Compound 2-2 (LT18-30-238) as a yellow solid.

Example 3: Synthesis of Compound 2-3 (LT18-30-346)

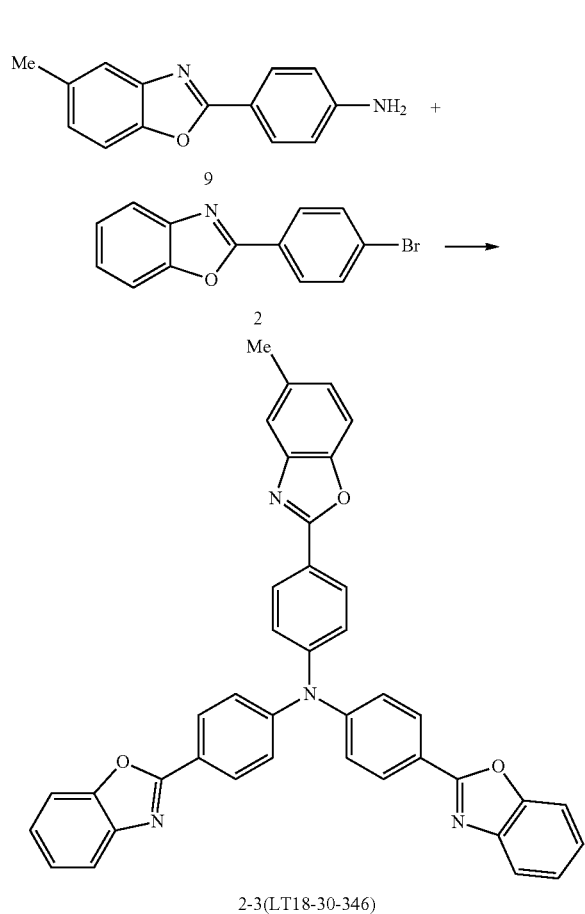

2-3(LT18-30-346)

1.5 g (6.69 mmol) of Intermediate 9, 5.50 g (20.10 mmol) of Intermediate 2, and 45 mL of xylene were placed in a 250 mL one-neck flask, and then 0.39 g (0.66 mmol) of Pd(dba)$_2$, 3.7 g (40.10 mmol) of sodium tert-butoxide, and 0.5 g (1.34 mmol) of tri-tert-butylphosphine (50 wt % in toluene) were added thereto. The mixture was allowed to react with stirring at 125-130° C. all day. After completion of the reaction, the reaction mixture was cooled to room temperature, filtered through a pad of celite using DCM, and distilled under reduced pressure to remove the solvent. The resulting residue was purified by SiO$_2$ column chromatography (EA:Hex=1:5) and slurried with acetone and hexane to remove impurities, giving 2.6 g (yield 63.7%) of Compound 2-3 (LT18-30-346) as a yellow solid.

Example 4: Synthesis of Compound 2-5 (LT18-30-292)

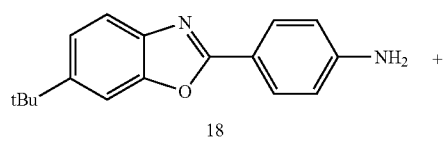

18

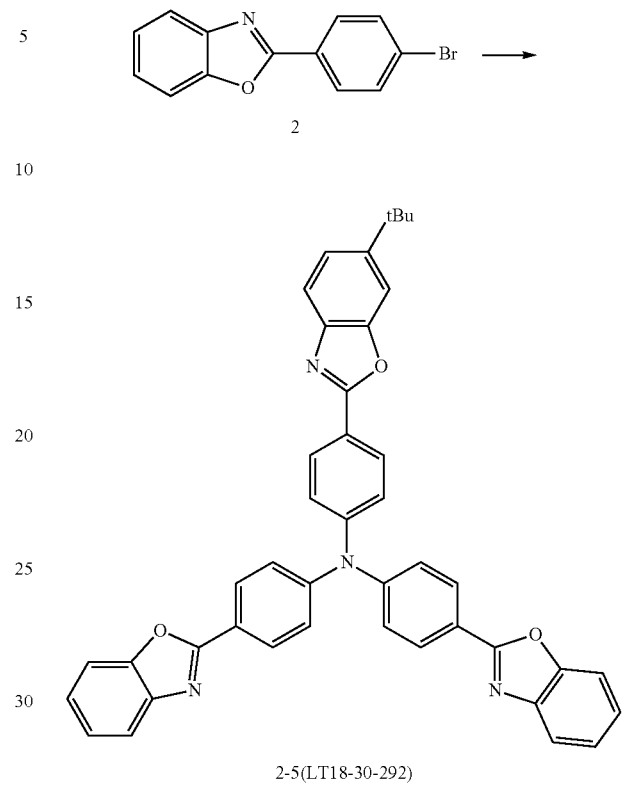

2-5(LT18-30-292)

2.4 g (9.05 mmol) of Intermediate 18, 6.0 g (21.72 mmol) of Intermediate 2, 520.0 mg (0.90 mmol) of Pd(dba)$_2$, 732.0 g (1.81 mmol) of 50% t-Bu$_3$P, 5.2 g (54.29 mmol) of NaOtBu, and 60 mL of xylene were mixed in a 250 mL one-neck flask. The mixture was allowed to react at 120° C. for 12 h. After completion of the reaction, the reaction mixture was cooled to room temperature, added with water, and extracted with chloroform. The solvent was removed under reduced pressure. The resulting residue was purified by silica gel column chromatography (Hex:EA=20:1), dissolved in acetone, and solidified while slowly adding dropwise MeOH to give 3.5 g (yield 58.9%) of Compound 2-5 (LT18-30-292) as a yellow solid.

Example 5: Synthesis of Compound 2-8 (LT18-30-252)

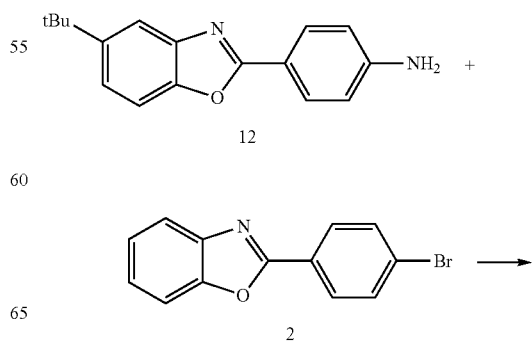

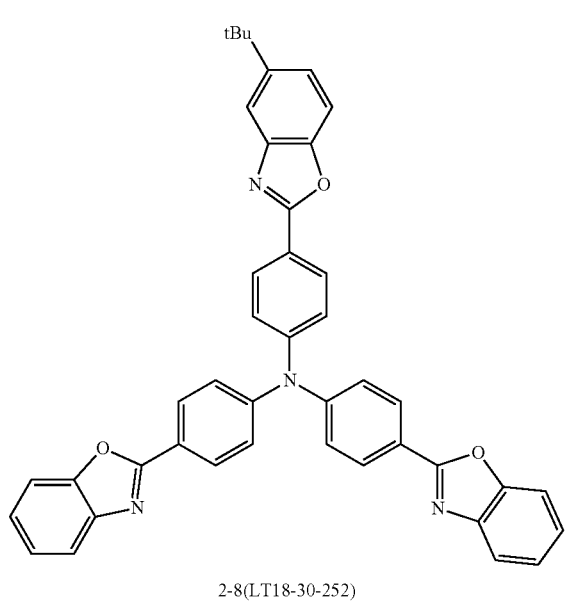

2-8(LT18-30-252)

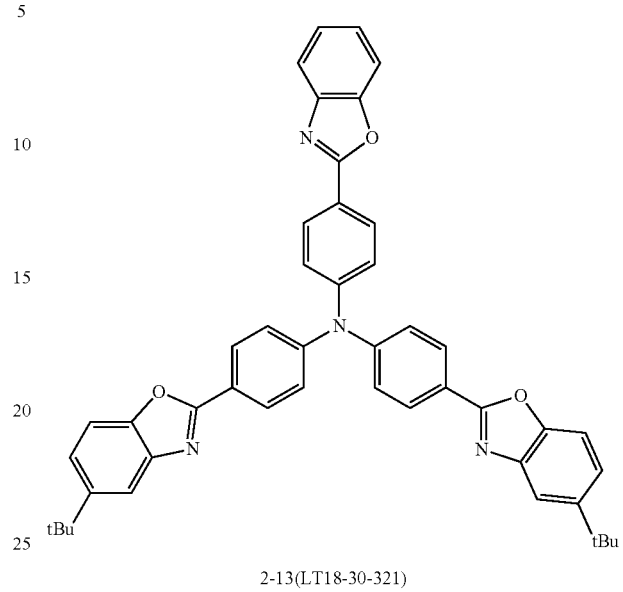

2-13(LT18-30-321)

2.0 g (7.51 mmol) of Intermediate 12, 5.2 g (18.77 mmol) of Intermediate 2, 432.0 mg (0.75 mmol) of Pd(dba)$_2$, 607.0 g (1.50 mmol) of 50% t-Bu$_3$P, 4.3 g (45.06 mmol) of NaOtBu, and 75 mL of xylene were mixed in a 250 mL one-neck flask. The mixture was allowed to react at 120° C. for 12 h. After completion of the reaction, the reaction mixture was cooled to room temperature, added with water, and extracted with chloroform. The solvent was removed under reduced pressure. The resulting residue was purified by silica gel column chromatography (Hex:EA=20:1) and solidified with methanol to give 2.4 g (yield 48.3%) of Compound 2-8 (LT18-30-252) as a yellow solid.

Example 6: Synthesis of Compound 2-13 (LT18-30-321)

1.5 g (7.13 mmol) of Intermediate 2, 5.7 g (17.12 mmol) of Intermediate 11, 410.0 mg (0.71 mmol) of Pd(dba)$_2$, 577 mg (1.43 mmol) of 50% t-Bu$_3$P, 4.1 g (42.81 mmol) of NaOtBu, and 70 mL of xylene were mixed in a 250 mL one-neck flask. The mixture was allowed to react at 120° C. for 12 h. After completion of the reaction, the reaction mixture was cooled to room temperature, added with water, and extracted with chloroform. The solvent was removed under reduced pressure. The resulting residue was purified by silica gel column chromatography (Hex:EA=20:1), dissolved in acetone, and solidified while slowly adding dropwise MeOH to give 2.4 g (yield 47.1%) of Compound 2-13 (LT18-30-321) as a yellow solid.

Example 7: Synthesis of Compound 2-14 (LT19-30-320)

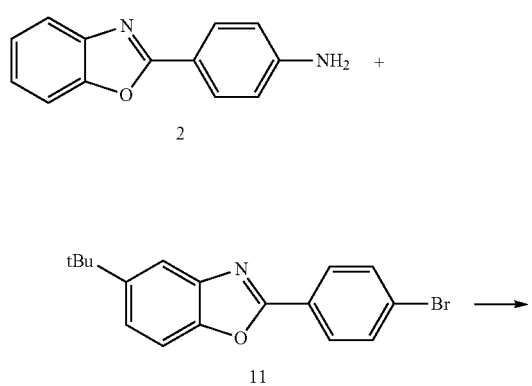

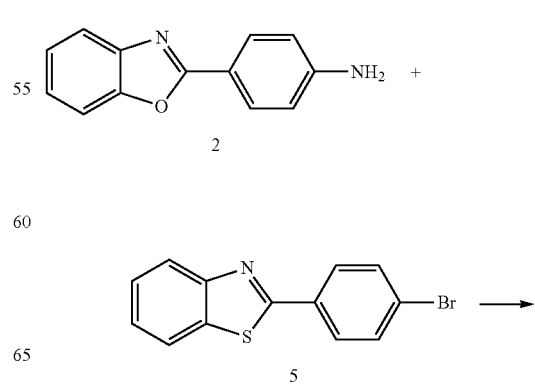

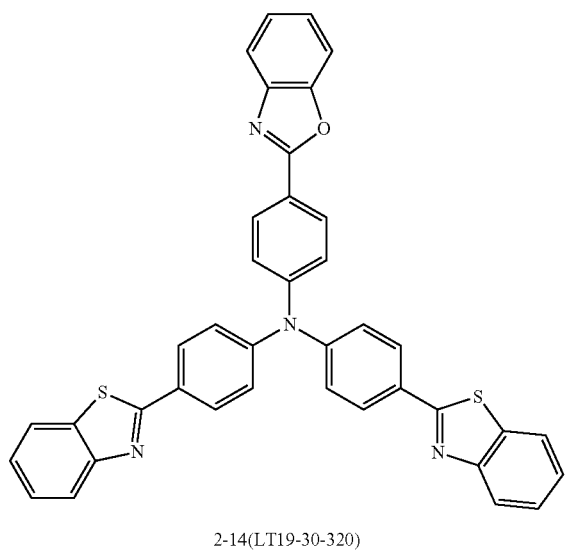

2-14(LT19-30-320)

1.8 g (8.47 mmol) of Intermediate 2, 7.3 g (25.40 mmol) of Intermediate 5, and 56 mL of xylene were mixed in a 250 mL one-neck flask, and then 0.5 g (0.85 mmol) of Pd(dba)$_2$, 4.9 g (50.80 mmol) of sodium tert-butoxide, and 0.7 g (1.69 mmol) of tri-tert-butylphosphine (50 wt % in toluene) were added thereto. The mixture was allowed to react with stirring at 125-130° C. for 4 h. After completion of the reaction, the reaction mixture was cooled to room temperature, filtered through a pad of celite using DCM under reduced pressure, and distilled under reduced pressure to remove the solvent. The resulting residue was purified by SiO$_2$ column chromatography (DCM:EA:HEX=1:1:5) to obtain a solid. Slurrying with acetone and hexane afforded a yellow solid. The solid was completely dissolved in CHCl$_3$ and recrystallized by slow addition of hexane to precipitate a solid. Filtration with hexane gave 3.2 g (yield 60.1%) of Compound 2-14 (LT19-30-320) as a yellow solid.

Example 8: Synthesis of Compound 2-15 (LT18-30-361)

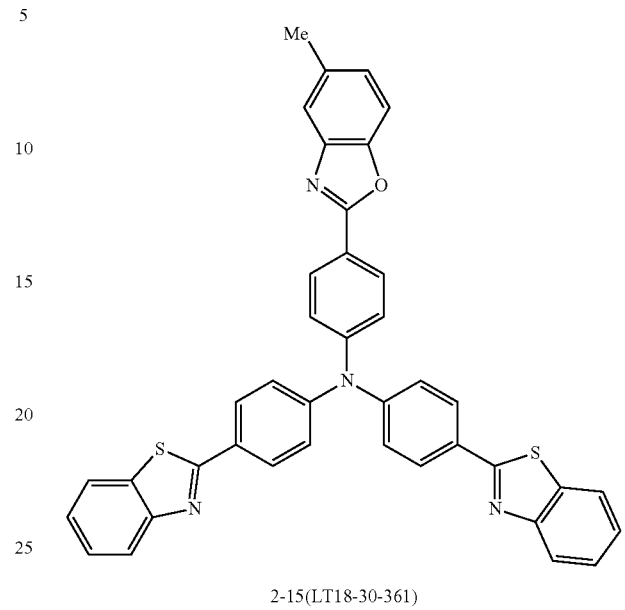

2-15(LT18-30-361)

1.9 g (8.47 mmol) of Intermediate 9, 7.3 g (25.40 mmol) of Intermediate 5, and 56 mL of xylene were mixed in a 250 mL one-neck flask, and then 0.5 g (0.85 mmol) of Pd(dba)$_2$, 4.9 g (50.80 mmol) of sodium tert-butoxide, and 0.7 g (1.69 mmol) of tri-tert-butylphosphine (50 wt % in toluene) were added thereto. The mixture was allowed to react with stirring at 125-130° C. for 4 h. After completion of the reaction, the reaction mixture was cooled to room temperature, filtered through a pad of celite using DCM under reduced pressure, and distilled under reduced pressure to remove the solvent. The resulting residue was purified by SiO$_2$ column chromatography (DCM:EA:HEX=1:1:5) to obtain a solid. Slurrying with acetone and hexane afforded a yellow solid. The solid was completely dissolved in CHCl$_3$ and recrystallized by slow addition of hexane to precipitate a solid. Filtration with hexane gave 3.4 g (yield 63.2%) of Compound 2-15 (LT18-30-361) as a yellow solid.

Example 9: Synthesis of Compound 2-16 (LT18-30-245)

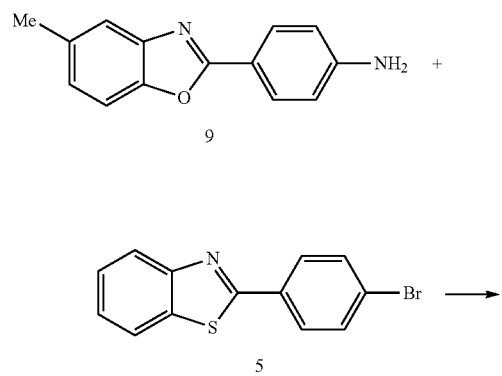

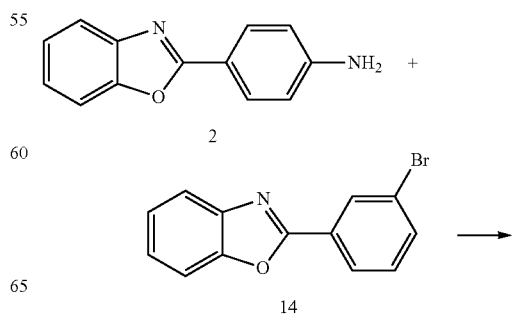

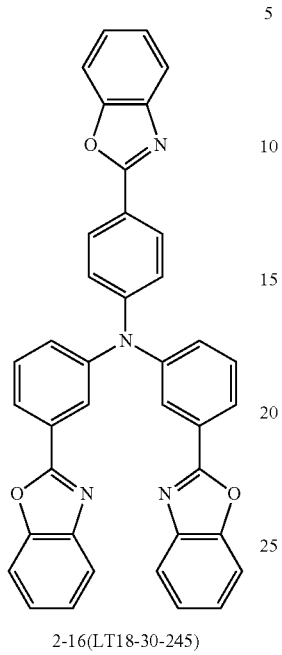

2-16(LT18-30-245)

1.5 g (7.13 mmol) of Intermediate 2, 4.9 g (17.84 mmol) of Intermediate 14, 410.0 mg (0.71 mmol) of Pd(dba)$_2$, 577.0 mg (1.43 mmol) of 50% t-Bu$_3$P, 4.1 g (42.81 mmol) of NaOtBu, and 50 mL of xylene were mixed in a 250 mL one-neck flask. The mixture was allowed to react at 120° C. for 12 h. After completion of the reaction, the reaction mixture was cooled to room temperature, filtered, washed with water and methanol, dried, purified by silica gel column chromatography (CHCl$_3$:EA=8:1), and solidified with methanol to give 1.6 g (yield 36.9%) of Compound 2-16 (LT18-30-245) as a yellow solid.

Example 10: Synthesis of Compound 2-18 (LT18-30-269)

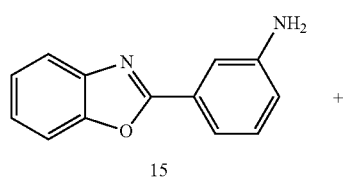

15

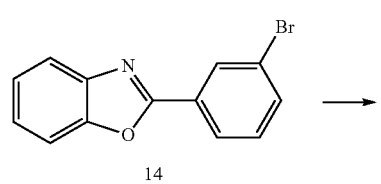

14

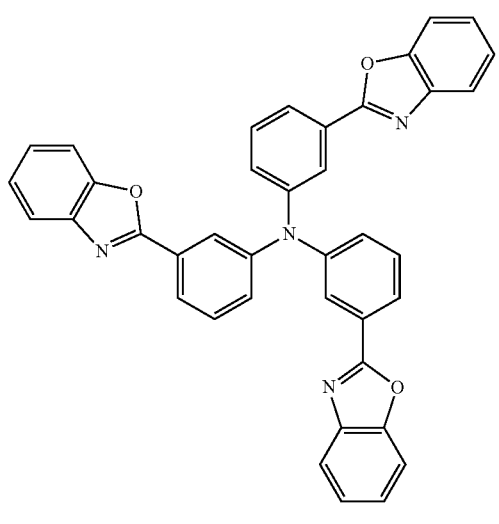

2-18(LT18-30-269)

1.8 g (8.56 mmol) of Intermediate 15, 6.1 g (22.30 mmol) of Intermediate 4, and 57 mL of xylene were mixed in a 250 mL one-neck flask, and then 0.5 g (0.86 mmol) of Pd(dba)$_2$, 4.9 g (51.40 mmol) of sodium tert-butoxide, and 0.7 g (1.71 mmol) of tri-tert-butylphosphine (50 wt % in toluene) were added thereto. The mixture was allowed to react with stirring at 125-130° C. all day. After completion of the reaction, the reaction mixture was cooled to room temperature to precipitate a solid. Filtration with hexane afforded a beige solid. The solid was dissolved in hot chloroform, purified by SiO$_2$ column chromatography (hot CHCl$_3$:EA=50:1), and slurried with CHCl$_3$ and hexane to give 3.1 g (yield 60.9%) of Compound 2-18 (LT18-30-269) as a pale yellow solid.

TEST EXAMPLES

The refractive indices (n) and extinction coefficients (k) of the inventive compounds were measured using a Filmetrics F20 instrument.

Test Examples 1-10: Preparation of Monolayer Films

A glass substrate (0.7T) was washed with ethanol, DI, and acetone (each for 10 min) and each of the compounds shown in Table 1 was deposited to a thickness of 800 Å thereon to form a monolayer film, which was used to measure the optical properties of the compound.

Comparative Test Example 1: Preparation of Monolayer Film (Glass/REF01 (80 nm))

Glass was treated with a 125 W oxygen plasma at 2×10$^{-2}$ Torr for 2 min. Thereafter, REF01 (80 nm) was deposited on the glass at a degree of vacuum of 9×10$^{-7}$ Torr and a rate of 1 Å/sec to form a monolayer film, which was used to measure the optical properties of the compound.

REF01

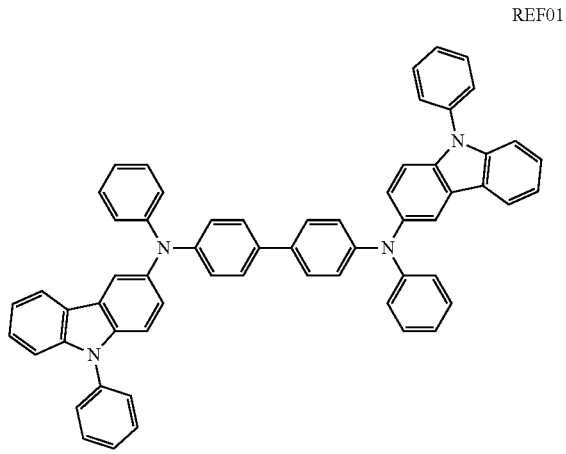 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]

The optical properties of the compounds used in Comparative Test Example 1 and Test Examples 1-10 are shown in Table 1.

The optical properties were the refractive indices at wavelengths of 450 nm and 620 nm and the absorption rate constants at a wavelength of 380 nm.

TABLE 1

| Properties | Compound | n (450 nm, 620 nm) | k (380 nm) |
|---|---|---|---|
| Comparative Test Example 1 | REF01 | 2.138, 1.971 | 0.274 |
| Test Example 1 | 2-1 (LT18-30-198) | 2.326, 2.018 | 0.679 |
| Test Example 2 | 2-2 (LT18-30-238) | 2.263, 1.997 | 0.598 |
| Test Example 3 | 2-3 (LT18-30-346) | 2.500, 2.071 | 0.759 |
| Test Example 4 | 2-5 (LT18-30-292) | 2.362, 2.008 | 0.532 |
| Test Example 5 | 2-8 (LT18-30-252) | 2.283, 1.953 | 0.658 |
| Test Example 6 | 2-13 (LT18-30-321) | 2.426, 2.018 | 0.693 |
| Test Example 7 | 2-14 (LT19-30-320) | 2.263, 2.000 | 0.598 |
| Test Example 8 | 2-15 (LT18-30-361) | 2.227, 1.980 | 0.634 |
| Test Example 9 | 2-16 (LT18-30-245) | 2.283, 1.953 | 0.658 |
| Test Example 10 | 2-18 (LT18-30-269) | 2.362, 2.008 | 0.532 |

As can be seen from the results in Table 1, the refractive indices (n) of all compounds used in Test Examples 1-10 at 450 nm were higher than that (2.138) of the compound (REF01) used in Comparative Test Example 1. That is, the refractive indices of the inventive compounds were high enough to secure wide viewing angles in the blue wavelength range.

In addition, the extinction coefficients (k) of all compounds used in Test Examples 1-10 at 380 nm were higher than that of the compound (REF01) used in Comparative Test Example 1. 380 nm is the upper limit of the UV region. These results concluded that the compounds used in Test Examples 1-10 can effectively absorb high energy UV light from external light sources to minimize damage to organic materials present in organic electroluminescent devices, contributing to a substantial improvement in the lifetime of the organic electroluminescent devices.

EXAMPLES

Device Fabrication

A transparent ITO electrode was used as an anode, 2-TNATA was used as a material for a hole injection layer, NPB was used as a material for a hole transporting layer, αβ-ADN and Pyene-CN were used as a host and a blue fluorescent dopant for an emission layer, respectively, Liq was used as a material for an electron injection layer, and Mg:Ag was used as a material for a cathode to fabricate a device. The structures of 2-TNATA, NPB, and αβ-ADN are as follow:

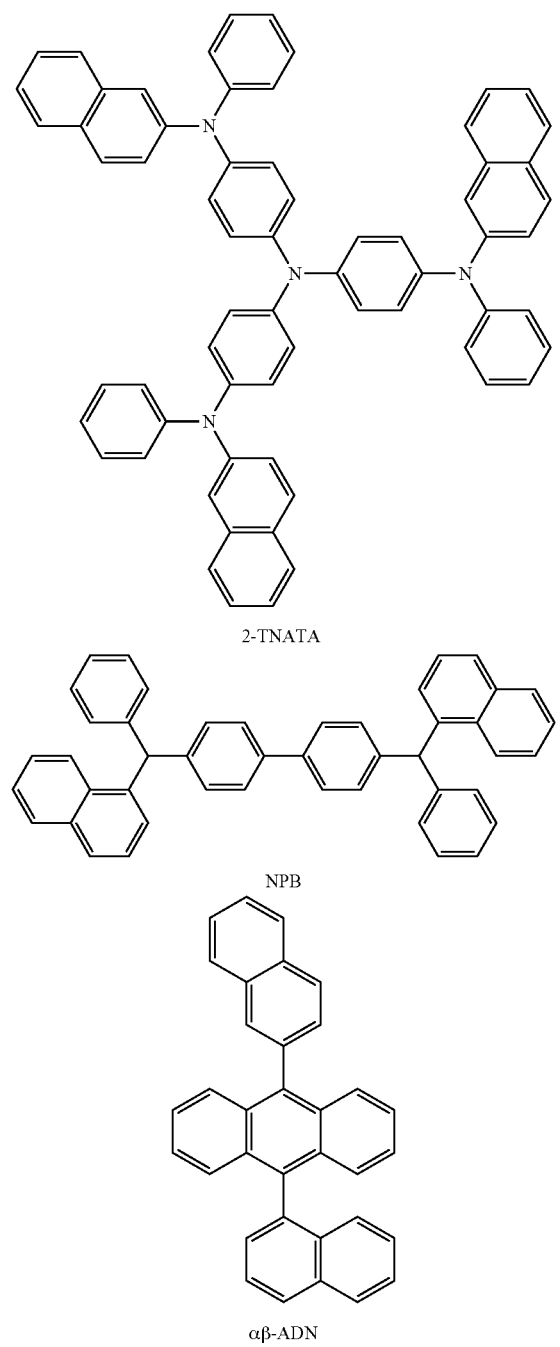

Comparative Example 1: ITO/2-TNATA (60 nm)/NPB (20 nm)/αβ-ADN: 10% pyrene-CN (30 nm)/Alq3 (30 nm)/Liq (2 nm)/Mg:Ag (1:9, 10 nm)/REF01 (60 nm)

ITO (180 nm), 2-TNATA (60 nm), NPB (20 nm), αβ-ADN:pyrene-CN 10% (30 nm), Alq$_3$ (30 nm), Liq (2 nm), and Mg:Ag (1:9, 10 nm) were deposited in this order to fabricate a blue fluorescent organic electroluminescent device. Before deposition of the organic materials, the ITO electrode was treated with a 125 W oxygen plasma at 2×10$^{-2}$ Torr for 2 min. The organic materials were deposited at a degree of vacuum of 9×10$^{-7}$ Torr. Liq was deposited at a rate of 0.1 Å/sec, αβ-ADN and pyrene-CN were deposited simultaneously at rates of 0.18 Å/sec and 0.02 Å/sec, respectively, and the other organic materials were deposited at a rate of 1 Å/sec. REF01 was used as a material for a capping layer. The device was sealed in a glove box filled with nitrogen gas to prevent contact with air and moisture. After a barrier was formed with an adhesive tape (3M), barium oxide as a moisture absorbent was placed to remove moisture and a glass plate was attached to the barrier.

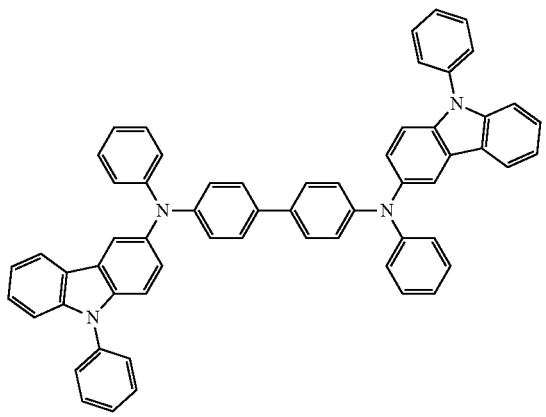

REF01

Examples 1-10

A device was fabricated in the same manner as in Comparative Example 1, except that the corresponding compound shown in Table 2 was used instead of REF01.

The electroluminescent properties of the organic electroluminescent devices fabricated in Comparative Example 1 and Examples 1-10 are shown in Table 2.

TABLE 2

| Properties | Compound | Driving voltage (V) | Efficiency (cd/A) | Lifetime (%) |
|---|---|---|---|---|
| Comparative Example 1 | REF01 | 6.60 | 5.10 | 88.92 |
| Example 1 | 2-1 (LT18-30-198) | 3.93 | 6.07 | 105.43 |
| Example 2 | 2-2 (LT18-30-238) | 3.81 | 5.65 | 98.79 |
| Example 3 | 2-3 (LT18-30-346) | 3.64 | 5.40 | 94.23 |
| Example 4 | 2-5 (LT18-30-292) | 4.05 | 5.72 | 108.17 |
| Example 5 | 2-8 (LT18-30-252) | 3.77 | 5.50 | 97.38 |
| Example 6 | 2-13 (LT18-30-321) | 4.14 | 6.97 | 99.52 |
| Example 7 | 2-14 (LT19-30-320) | 3.81 | 5.65 | 98.79 |
| Example 8 | 2-15 (LT18-30-361) | 3.96 | 6.81 | 104.71 |
| Example 9 | 2-16 (LT18-30-245) | 3.93 | 5.77 | 101.48 |
| Example 10 | 2-18 (LT18-30-269) | 3.66 | 5.57 | 95.67 |

The results in Table 2 reveal that the inventive tribenzazole amine derivatives are suitable for use as materials for capping layers of organic electronic devices (including organic electroluminescent devices). In addition, organic electronic devices (including organic electroluminescent devices) using the inventive tribenzazole amine derivatives are excellent in terms of efficiency, driving voltage, and stability. Particularly, the inventive compounds have high efficiencies due to their outstanding ability to form microcavities.

Surprisingly, the compound of Formula 1 has desirable characteristics for use as a material for a capping layer of an OLED.

Based on its characteristics, the compound of the present invention can be used in organic electronic devices for industrial applications.

The above synthesis examples are merely illustrative and the reaction conditions may vary as required. The compounds according to exemplary embodiments of the present invention may be substituted with various substituents using suitable methods and materials known in the art. The introduction of various substituents to the core structure of the compound represented by Formula 1 allows the substituted compounds to have characteristics suitable for use in organic electroluminescent devices.

INDUSTRIAL APPLICABILITY

The tribenzazole amine derivative of the present invention can be used as a material for an organic layer and/or a capping layer of an organic electroluminescent device to improve the quality of the organic electroluminescent device.

When the compound of the present invention is used in a capping layer of an organic electroluminescent device, the optical properties of the compound ensure an improvement in the lifetime of the organic electroluminescent device while allowing the organic electroluminescent device to exhibit its original characteristics.

The invention claimed is:

1. A tribenzazole amine compound represented by Formula 1:

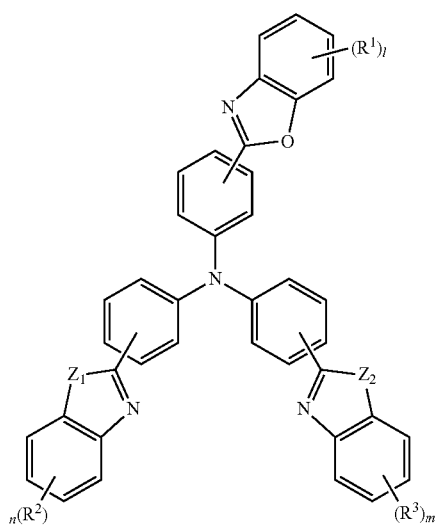

Formula 1 wherein $Z_1$ and $Z_2$ are each independently O or S, $R^1$, $R^2$, and $R^3$ are identical to or different from each other and are each independently hydrogen or unsubstituted alkyl, and l, n, and m are independently an integer from 0 to 4.

2. The tribenzazole amine compound according to claim 1, wherein the tribenzazole amine compound is selected from compounds represented by the following Formula 2-1 to Formula 2-18:
2-1
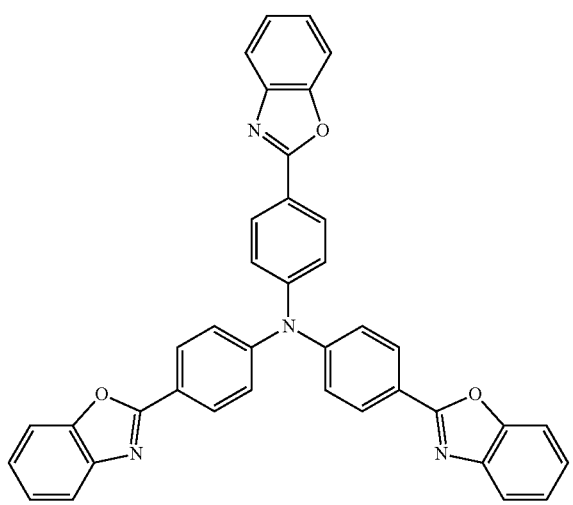
2-2
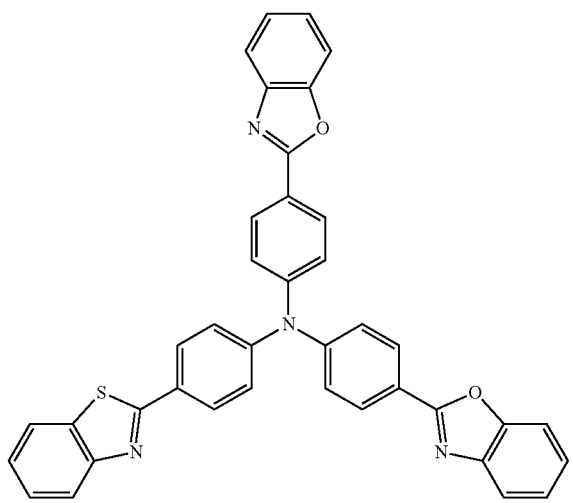
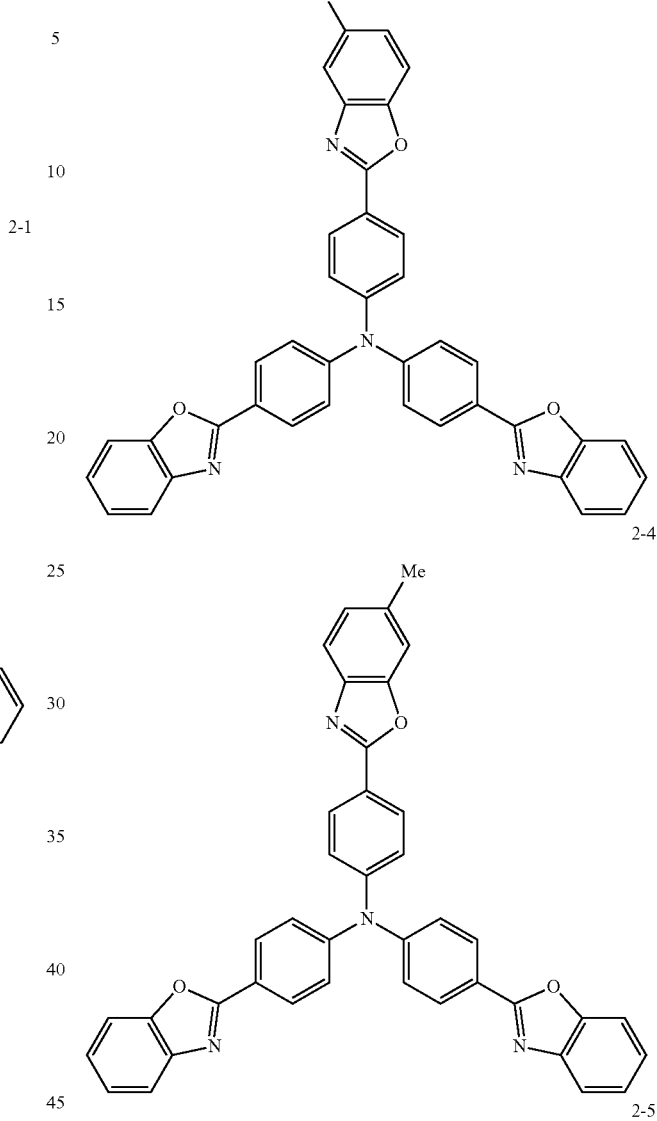

2-6
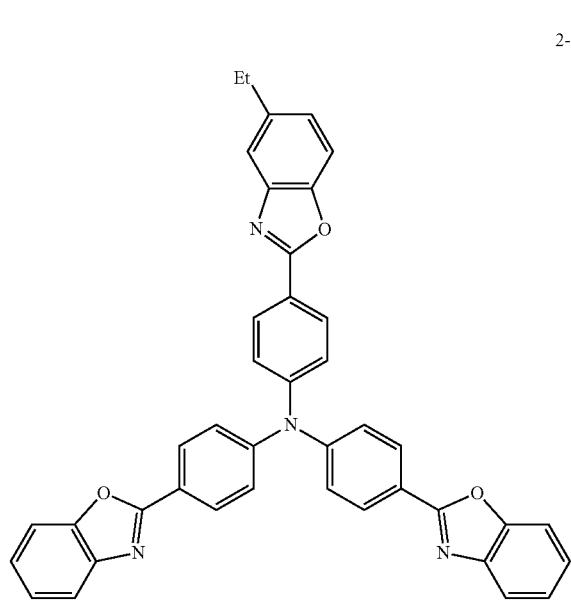
2-8
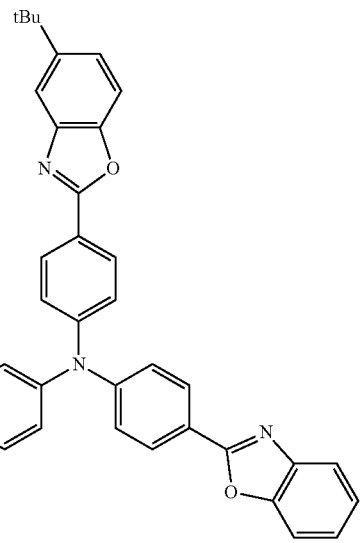
2-9
2-7
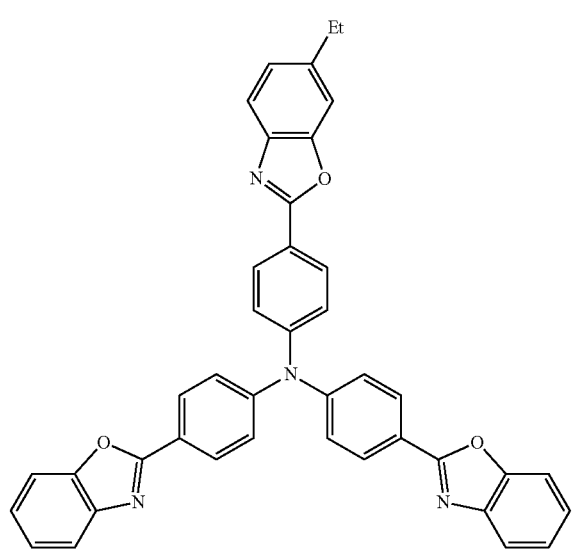
2-10

2-11
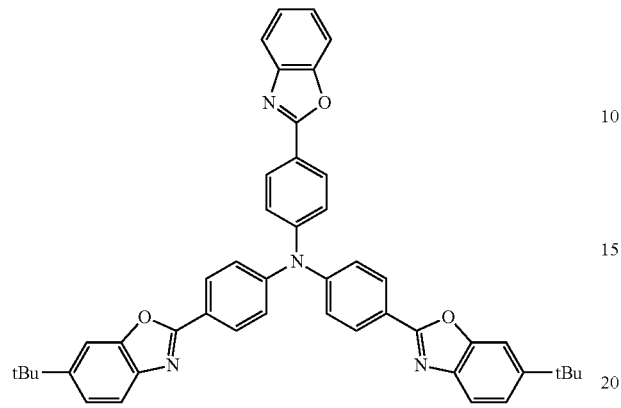
2-12
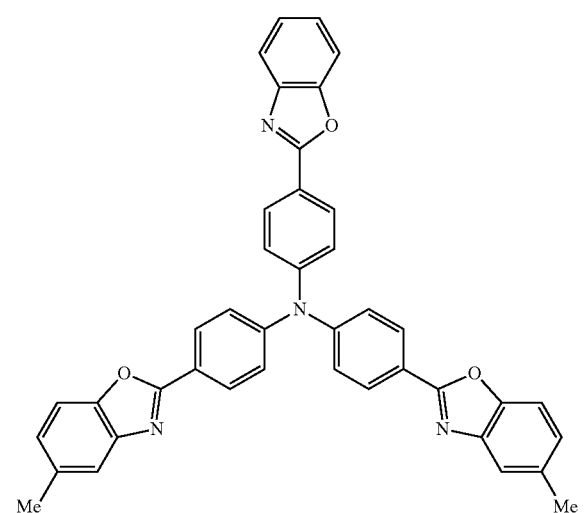
2-13
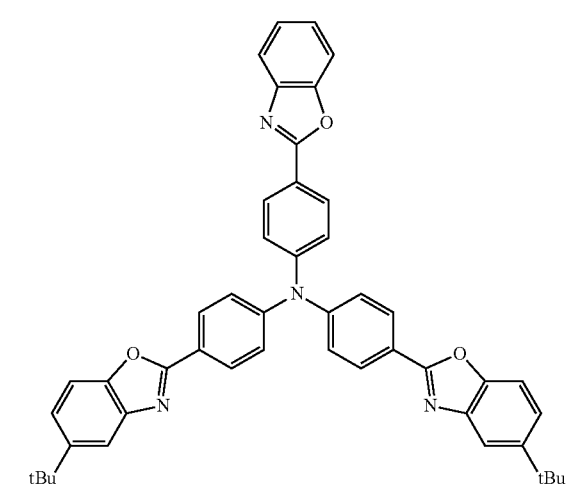
2-14
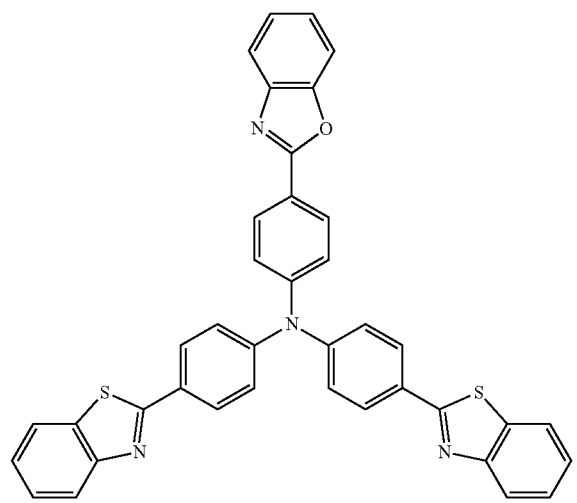
2-15
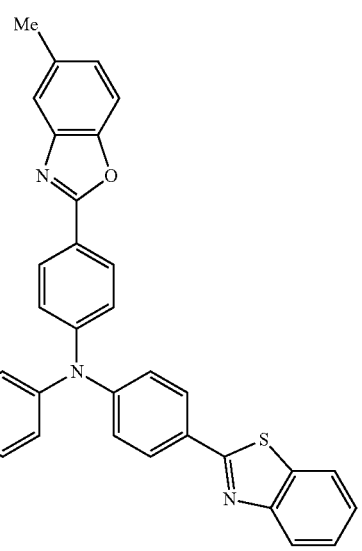

2-16

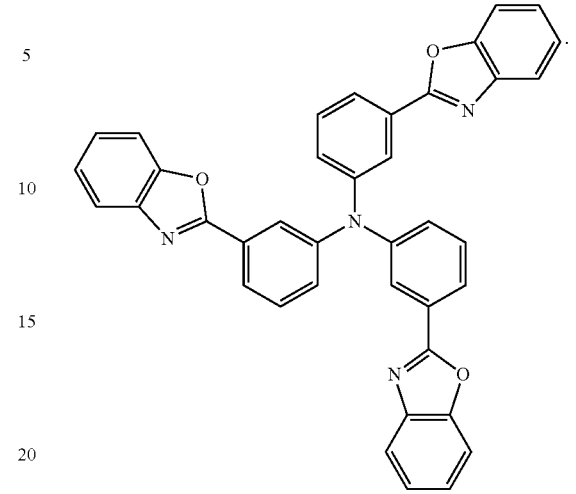

2-18

2-17

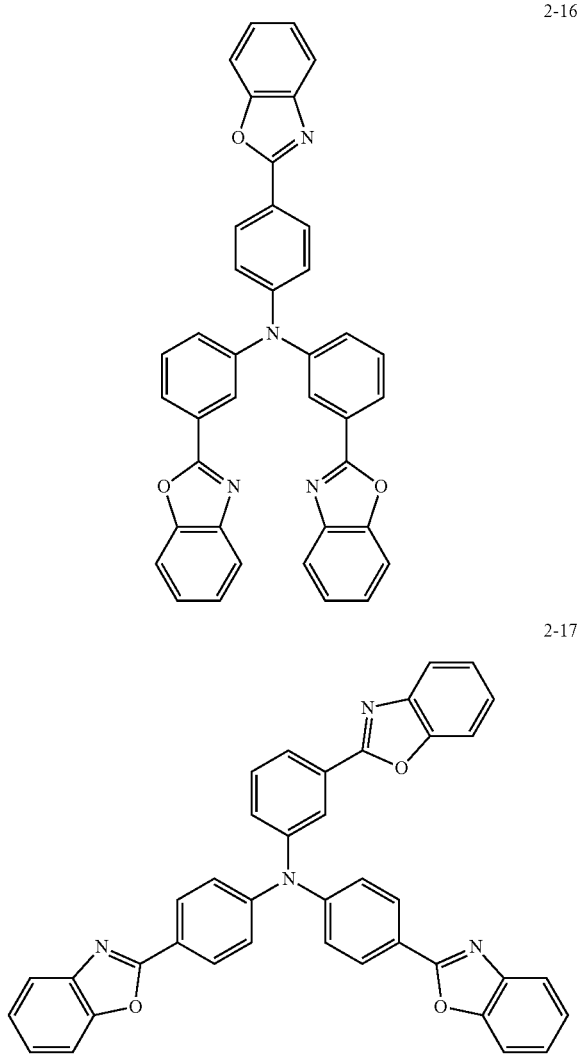

3. An organic electroluminescent device comprising a first electrode, an organic layer consisting of a plurality of layers arranged on the first electrode, a second electrode arranged on the organic layer, and a capping layer arranged on the second electrode, wherein the capping layer comprises the tribenzazole amine compound according to claim 1.

4. The organic electroluminescent device according to claim 3, wherein the organic layer comprises a hole injection layer, a hole transporting layer, an emission layer, an electron transporting layer, and an electron injection layer.

5. An organic electroluminescent device comprising a first electrode, an organic layer consisting of a plurality of layers arranged on the first electrode, a second electrode arranged on the organic layer, and a capping layer arranged on the second electrode, wherein the capping layer comprises the tribenzazole amine compound according to claim 2.

6. The organic electroluminescent device according to claim 5, wherein the organic layer comprises a hole injection layer, a hole transporting layer, an emission layer, an electron transporting layer, and an electron injection layer.

* * * * *